United States Patent [19]
Saiga et al.

[11] Patent Number: 6,090,783
[45] Date of Patent: Jul. 18, 2000

[54] DNA MOLECULE RELATING TO SUPPRESSION OF GENE EXPRESSION AND NOVEL PROTEIN

[75] Inventors: Akihiko Saiga, Katano; Satoshi Orita, Kobe; Hisanaga Igarashi, Osaka; Kouichi Okumura; Gaku Sakaguchi, both of Takatsuki, all of Japan

[73] Assignee: Shionogi & Co., Ltd., Osaka, Japan

[21] Appl. No.: 09/121,321

[22] Filed: Jul. 23, 1998

Related U.S. Application Data

[62] Division of application No. 08/933,803, Sep. 19, 1997, which is a continuation-in-part of application No. 08/913,665, filed as application No. PCT/JP96/00719, Mar. 19, 1996.

[30] Foreign Application Priority Data

Mar. 24, 1995 [JP] Japan .................................. 7-066559
Apr. 27, 1995 [JP] Japan .................................. 7-104299

[51] Int. Cl.$^7$ ........................ A61K 38/00; C07K 14/435; C07K 14/47
[52] U.S. Cl. ............................................. 514/12; 530/350
[58] Field of Search .................................. 530/350, 358, 530/356; 514/12

[56] References Cited

U.S. PATENT DOCUMENTS 4,778,756  10/1988  Yoshida et al. .......................... 435/320

FOREIGN PATENT DOCUMENTS 0 113 078 B1  7/1984  European Pat. Off. ........ C12N 15/00
59-104325  6/1984  Japan .............................. A61K 39/12

OTHER PUBLICATIONS

Adachi, A. et al., "Production of Acquired Immunodeficiency Syndrome–Associated Retrovirus in Human and Nonhuman Cells Transfected with an Infectious Molecular Clone," *Journal of Virology*, 59, 2, pp. 284–291 (1986).

Chang, D.D. et al., "Messenger RNA Transport and HIV rev Regulation," *Science*, 249, pp. 614–615 (1990).

Chomczynski, P. et al., "Single–Step Method of RNA Isolation by Acid Guanidinium Thiocyanate–Phenol–Chloroform Extraction," *Analytical Biochemistry*, 162, pp. 156–159 (1987).

Constantinou–Deltas, C.D. et al., "The Identification and Characterization of KRAB–Domain–Containing Zinc Finger Proteins," *Genomics*, 12, pp. 581–589 (1992).

Fordis, C.M. et al., "Use of the Cat Reporter Gene for Optimization of Gene Transfer into Eukaryotic Cells," *Methods in Enzymology*, 151, pp. 382–397 (1987).

Hanly, S.M. et al., "Comparative Analysis of the HTLV–I Rex and HIV–1 Rev trans–Regulatory Proteins and Their RNA Response Elements," *Genes & Development*, 3, pp. 1534–1544 (1989).

Hidaka, M. et al., "Post–Transcriptional Regulator (rex) of HTLV–1 Initiates Expression of Viral Structural Proteins but Suppresses Expression of Regulatory Proteins," *The EMBO Journal*, 7, 2, pp. 519–523 (1988).

Inoue, J. et al., "Trancriptional (p40$^x$) and Post–Transcriptional (p27$^{x-III}$) Regulators Are Required for the Expression and Replication of Human T–Cell Leukemia Virus Type I Genes," *Proc. Natl. Acad. Sci. USA*, 84, pp. 3653–3657 (1987).

Kashanchi, F. et al., "Involvement of Transcription Factor YB–1 in Human T–Cell Lymphotropic Virus Type I Basal Gene Expression," *Journal of Virology*, 68, 1, pp. 561–565 (1994).

Kiyokawa, T. et al., "p27$^{x-III}$ and p21$^{x-III}$, Proteins Encoded by the pX Sequence of Human T–Cell Leukemia Virus Type I," *Proc. Natl. Acad. Sci. USA*, 82, pp. 8359–8363 (1985).

Margolin, J.F. et al., "Krüppel–Associated Boxes Potent Transcriptional Repression Domains," *Proc. Natl. Acad. Sci. USA*, 91, pp. 4509–4513 (1994).

Numoto, M. et al., "Trancriptional Repressor ZF5 Identifies a New Conserved Domain in Zinc Finger Proteins," *Nucleic Acids Research*, 21, 16, pp. 3767–3775 (1993).

Okumura, K. et al., "Autoantigen Ku Protein Is Involved in DNA Binding Proteins which Recognize the U5 Repressive Element of Human T–Cell Leukemia Virus Type I Long Terminal Repeat," *FEBS Letters*, 356, pp. 94–100 (1994).

Orita, S. et al., "A Novel Alternatively Spliced Viral mRNA Transcribed in Cells Infected with Human T Cell Leukemia Virus Type 1 is Mainly Responsible for Expressing p21X Protein," *FEBS Letters*, 295, pp. 127–134 (1991).

Orita, S. et al., "Human T Cell Leukaemia Virus Type 1 p21X mRNA: Constitutive Expression in Peripheral Blood Mononuclear Cells of Patients with Adult T Cell Leukaemia," *Journal of General Virology*, 73, pp. 2283–2289 (1992).

Orita, S. et al., "Identification of Novel Singly Spliced pX mRNA Transcripts Common to All Human T–Cell Leukemia Virus Type 1–Related Retroviruses," *Virus Genes*, 7, pp. 197–204 (1993).

(List continued on next page.)

*Primary Examiner*—Ponnathapu Achutamurthy
*Assistant Examiner*—Maryam Monshipouri
*Attorney, Agent, or Firm*—Fish & Neave; James F. Haley, Jr.; Jennifer T. Weissman

[57] ABSTRACT

A DNA molecule having a gene expression repressing function derived from human T-cell leukemia virus type I (HTLV-I) existing in a region which is missing in a mutant provirus that is expressing p21Xm RNA but exists in the genome of a complete provirus, and a plasmid including the DNA molecule are provided. Furthermore, a novel protein (TRP-1) which specifically binds to U5RE and a structural gene for the protein is provided, which can be useful for elucidation of the transcription repression activity and elucidation of the oncogenesis mechanism of neurocytes, in which a transcriptional repressive region (U5RE) existing in the U5 region of human T-cell leukemia virus type I gene LTR is involved. Furthermore, an expression vector including the gene, a transformant into which the expression vector is introduced, and a process for producing the TRP-1 protein using the transformant are provided.

5 Claims, 14 Drawing Sheets

OTHER PUBLICATIONS

Orita, S. et al., "p21X mRNA Is Expressed as a Singly Spliced pX Transcript from Defective Provirus Genomes Having a Partial Deletion of the pol–env Region in Human T–Cell Leukemia Virus Type 1–Infected Cells," *Nucleic Acids Research*, 21, 16, pp. 3799–3807 (1993).

Sagata, N. et al., "Complete Nucleotide Sequence of the Genome of Bovine Leukemia Virus: Its Evolutionary Relationship to Other Retroviruses," *Proc. Natl. Acad. Sci. USA*, 82, pp. 677–681 (1985).

Seiki, M. et al., "Human Adult T–Cell Leukemia Virus: Complete Nucleotide Sequence of the Provirus Genome Integrated in Leukemia Cell DNA," *Proc. Natl. Acad. Sci. USA*, 80, pp. 3618–3622 (1983).

Seiki, M. et al., "The U5 Sequence Is a cis–Acting Repressive Element for Genomic RNA Expression of Human T Cell Leukemia Virus Type I," *Virology*, 176, pp. 81–86 (1990).

Seiki, M. et al., "Two cis–Acting Elements Responsible for Posttranscriptional Trans–Regulation of Gene Expression of Human T–Cell Leukemia Virus Type I," *Proc. Natl. Acad. Sci. USA*, 85, pp. 7124–7128 (1988).

Shimotohno, K., et al., "Complete Nucleotide Sequence of an Infectious Clone of Human T–Cell Leukemia Virus Type II: An Open Reading Frame for the Protease Gene," *Proc. Natl. Acad. Sci. USA*, 82, pp. 3101–3105 (1985).

Toyoshima, H. et al., "Secondary Structure of the Human T–Cell Leukemia Virus Type 1 rex–Responsive Element Is Essential for rex Regulation of RNA Processing and Transport of Unspliced RNAs," *Journal of Virology*, 64, 6, pp. 2825–2832 (1990).

Weiss et al., "Supplement: Human T–Cell Retroviruses," *RNA Tumor Viruses*, pp. 405–485 (1985).

Witzgall, R. et al., "Kid–1, A Putative Renal Transcription Factor: Regulation During Ontogeny and in Response to Ischemia and Toxic Injury," *Molecular and Cellular Biology*, 13, 3, pp. 1933–1942 (1993).

Witzgall, R. et al., "The Krüppel–Associated Box–A (KRAB–A) Domain of Zinc Finger Proteins Mediates Transcriptional Repression," *Proc. Natl. Acad. Sci. USA*, 91, pp. 4514–4518 (1994).

Xu, X. et al., "Transcriptional Suppression of the Human T–Cell Leukemia Virus Type I Long Terminal Repeat Occurs by an Unconventional Interaction of a CREB Factor with the R Region," *Molecular and Cellular Biology*, 14, 8, pp. 5371–5383 (1994).

Bellefroid et al., DNA, 8, 377–387, Jun. 1989.

Garcia–Cantalejo et al., Yeast, 10, 231–245, Jun. 1994.

Okumura et al., FEBS Letters, 356, 94–100, Dec. 1994.

McGeoch et al., J. Gen. Virol., 69, 1531–1574, Jul. 1988.

Lewin, R., "When Does Homology Mean Something Else?," *Science*, 237, p. 1570 (1987).

Malik, K.T.A. et al., "Molecular Cloning and Complete Nucleotide Sequence of an Adult T Cell Leukaemia Virus/Human T Cell Leukaemia Virus Type I (ATLV/HTLV–I) Isolate of Caribbean Origin: Relationship to Other Members of the ATLV/HTLV–I Subgroup," *J. Gen. Virol.*, 69, pp. 1695–1710 (1988).

Öberg, B. et al., "Screening for New Agents," *Eur. J. Clin. Microbiol. Infect Dis.*, 9(7), pp. 466–471 (1990).

Reeck, G.R. et al., "'Homology' in Proteins and Nucleic Acids: A Terminology Muddle and a Way out of It," *Cell*, 50, p. 667 (1987).

Yarchoan, R. et al., "Correlations between the in Vitro and in Vivo Activity of Anti–HIV Agents: Implications for Future Drug Development," *J. Enzyme Inhibition*, 6, pp. 99–111 (1992).

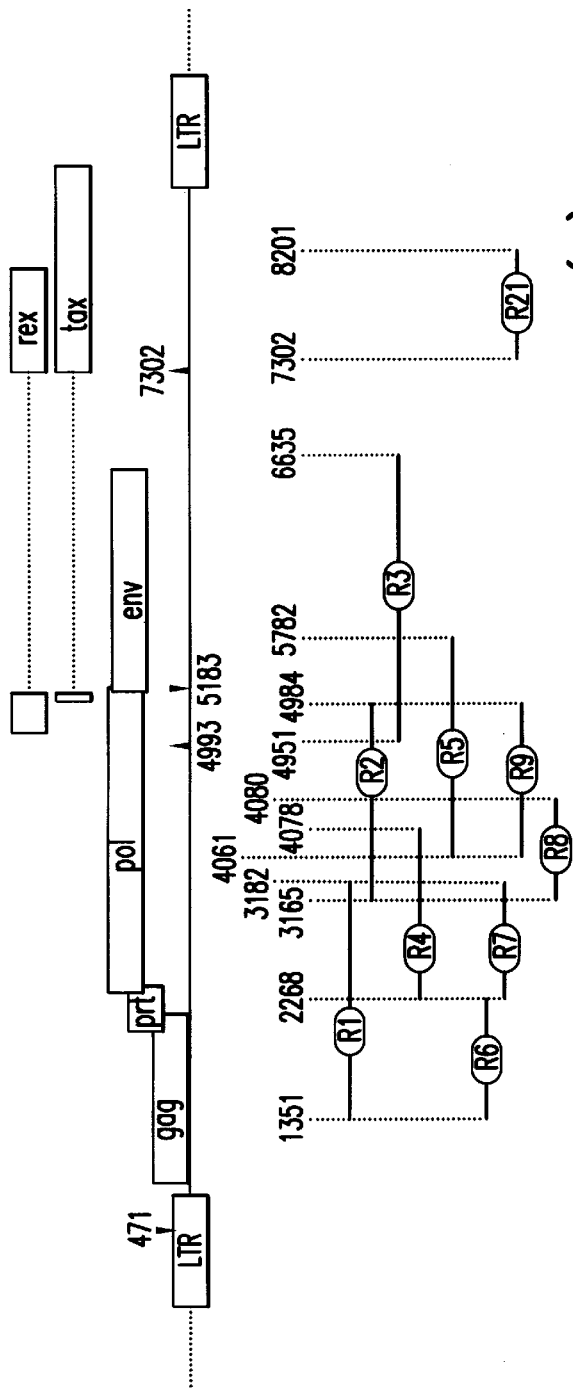
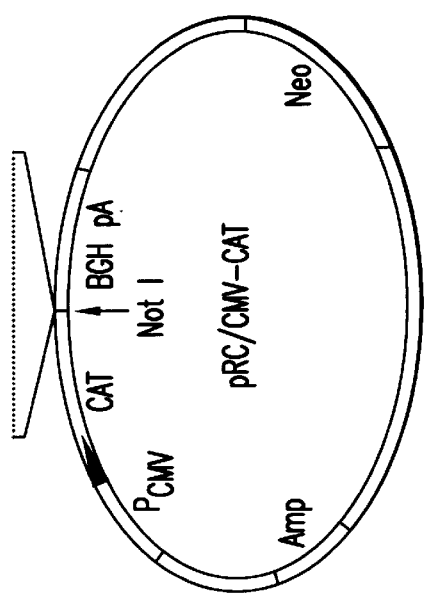
FIG.1(a)
FIG.1(b)

Zn fingers

```
518  YSCPECGKSFGVRKSLIIHHRSHTKERP  545
546  YECAECEKSFNCHSGLIRHQMTHRGERP  573
574  YKCSECEKTYSRKEHLQNHQRLHTGERP  601
602  FQCALCGKSFIRKQNLLKHQRIHTGERP  629
630  YTCGECGKSFRYKESLKDHLTVHSGGPG  657
```

Consensus sequence  Y C ECGK F    L  H   HTGERP
                    F

FIG.11

KRAB-A domain

NSW 2    196  VPVTFVDIAVYFSEDEWKNLDEWQKELYNNLVKENYKTLMSL  236

KID 1    12   VSVTFEDVAVLFTRDEWKKLDLSQRSLYREVMLENYSNLASM  28

Consensus sequence 1  esvtFeDVaveFsleEWqcLdpaQrnLYrdVMLENyrnlvsl
Consensus sequence 2  .L.F.DV...F..EEW..LD..Q..LYR.VMLENY..LV..

KRAB-B domain

NSW 2    237  DAEGS-VPKPDAPVQAEPREEPCVW  261

KID 1    29   AGFLFTKPKVISLLQQGEDPWQV  53

Consensus sequence  .G....KPDL...LE.....W..

FIG.12

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 9045 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: human (ix) FEATURE:
       (A) NAME/KEY: LTR
       (B) LOCATION: 1..757

(ix) FEATURE:
       (A) NAME/KEY: polyA_signal
       (B) LOCATION: 8584..8589

(ix) FEATURE:
       (A) NAME/KEY: LTR
       (B) LOCATION: 8278..9032

(xi) SEQUENCE DESCRIPTION: SEQ ID NO:1:

```
TGACAATGAC CATGAGCCCC AAATATCCCC CGGGGGCTTA GAGCCTCCCA GTGAAAAACA      60

TTTCCGAGAA ACAGAAGTCT GAAAAGGTCA GGGCCCAGAC TAAGGCTCTG ACGTCTCCCC     120

CCGGAGGGCA GCTCAGCACC GGCTCGGGCT AGGCCCTGAC GTGTCCCCCT GAAGACAAAT     180

CATAAGCTCA GACCTCCGGG AAGCCACCAA GAACCACCCA TTTCCTCCCC ATGTTTGTCA     240
```

```
AGCCGTCCTC AGGCGTTGAC GACAACCCCT CACCTCAAAA AACTTTTCAT GGCACGCATA      300

TGGCTCAATA AACTAGCAGG AGTCTATAAA AGCGTGGAGA CAGTTCAGGA GGGGGCTCGC      360

ATCTCTCCTT CACGCGCCCG CCGCCCTACC TGAGGCCGCC ATCCACGCCG GTTGAGTCGC      420

GTTCTGCCGC CTCCCGCCTG TGGTGCCTCC TGAACTGCGT CCGCCGTCTA GGTAAGTTTA      480

AAGCTCAGGT CGAGACCGGG CCTTTGTCCG GCGCTCCCTT GGAGCCTACC TAGACTCAGC      540

CGGCTCTCCA CGCTTTGCCT GACCCTGCTT GCTCAACTCT ACGTCTTTGT TTCGTTTTCT      600

GTTCTGCGCC GTTACAGATC GAAAGTTCCA CCCCTTTCCC TTTCATTCAC GACTGACTGC      660

CGGCTTGGCC CACGGCCAAG TACCGGCGAC TCCGTTGGCT CGGAGCCAGC GACAGCCCAT      720

CCTATAGCAC TCTCAGGAGA GAAATTTAGT ACACAGTTGG GGGCTCGTCC GGGATACGAG      780

CGCCCCTTTA TTCCCTAGGC AATGGGCCAA ATCTTTTCCC GTAGCGCTAG CCCTATTCCG      840

CGACCGCCCC GGGGGCTGGC CGCTCATCAC TGGCTTAACT TCCTCCAGGC GGCATATCGC      900

CTAGAACCCG GTCCCTCCAG TTACGATTTC CACCAGTTAA AAAAATTTCT TAAAATAGCT      960

TTAGAAACAC CGGCTCGGAT CTGTCCCATT AACTACTCCC TCCTAGCCAG CCTACTCCCA     1020

AAAGGATACC CCGGCCGGGT GAATGAAATT TTACACATAC TCATCCAAAC CCAAGCCCAG     1080

ATCCCGTCCC GTCCCGCGCC ACCGCCGCCG TCATCCCCCA CCCACGACCC CCGGATTCT      1140

GATCCACAAA TCCCCCCTCC CTATGTTGAG CCTACGGCCC CCCAAGTCCT TCCAGTCATG     1200

CATCCACATG GTGCTCCTCC TAACCATCGC CCATGGCAAA TGAAAGACCT ACAGGCCATT     1260

AAGCAAGAAG TCTCCCAAGC AGCCCCTGGG AGCCCCCAGT TTATGCAGAC CATCCGGCTT     1320

GCGGTGCAGC AGTTTGACCC CACTGCCAAA GACCTCCAAG ACCTCCTGCA GTACCTTTGC     1380

TCCTCCCTCG TGGCTTCCCT CCATCACCAG CAGCTAGATA GCCTTATATC AGAGGCCGAA     1440

ACCCGAGGTA TTACAGGTTA TAACCCATTA GCCGGTCCCC TCCGTGTCCA AGCCAACAAT     1500

CCACAACAAC AAGGATTAAG GCGAGAATAC CAGCAACTCT GGCTCGCCGC CTTCGCCGCC     1560

CTGCCGGGGA GTGCCAAAGA CCCTTCCTGG GCCTCTATCC TCCAAGGCCT GGAGGAGCCT     1620

TACCACGCCT TCGTAGAACG CCTCAACATA GCTCTTGACA ATGGGCTGCC AGAAGGCACG     1680

CCCAAAGACC CCATCTTACG TTCCTTAGCC TACTCCAATG CAAACAAAGA ATGCCAAAAA     1740

TTACTACAGG CCCGAGGACA CACTAATAGC CCTCTAGGAG ATATGTTGCG GGCTTGTCAG     1800

ACCTGGACCC CCAAAGACAA AACCAAAGTG TTAGTTGTCC AGCCTAAAAA ACCCCCCCCA     1860

AATCAGCCGT GCTTCCGGTG CGGGAAAGCA GGCCACTGGA GTCGGACTG CACTCAGCCT      1920

CGTCCCCCCC CCGGGCCATG CCCCCTATGT CAAGACCCAA CTCACTGGAA GCGAGACTGC     1980

CCCCGCCTAA AGCCCACTAT CCCAGAACCA GAGCCAGAGG AAGATGCCCT CCTATTAGAC     2040

CTCCCCGCTG ACATCCCACA CCCAAAAAAC TTCATAGGGG GGGAGGTTTA ACCTCCCCCC     2100

CCACATTACA GCAAGTCCTT CCTAACCAAG ACCCAGCATC TATTCTGCCA GTTATACCGT     2160

TAGATCCCGC CCGTCGGCCC GTAATTAAAG CCCAGGTTGA CACCCAGACC AGCCACCCAA     2220

AGACTATCGA AGCTTTACTA GATACAGGAG CAGACATGAC AGTCCTTCCG ATAGCCTTGT     2280

TCTCAAGTAA TACTCCCTCA AAAATACATC CGTATTAGGG GCAGGGGCC AAACCCAAGA      2340

TCACTTTAAG CTCACCTCCC TTCCTGTGCT AATACGCCTC CCTTTCCGGA CAACGCCTAT     2400

TGTTTTAACA TCTTGCCTAG TTGATACCAA AAACAACTAG GCCATCATAG GTCGTGATGC     2460

CTTACAACAA TGCCAAGGCG TCCTGTACCT CCCTGAGGCA AAAAGGCCGC CTGTAATCTT     2520

GCCAATACAG GCGCCAGCCG TCCTTGGGCT AGAACACCTC CCAAGGCCCC CCGAAATCAG     2580
```

```
CCAGTTCCCT TTAAACCAGA ACGCCTCCAG GCCTTGCAAC ACTTGGTCCG GAAGGCCCTG    2640

GAGGCAGGCC ATATCGAACC CTACACCGGG CCAGGGAATA ACCCAGTATT CCCAGTTAAA    2700

AAGGCCAATG GAACCTGGCG ATTCATCCAC GACCTGCGGG CCACTAACTC TCTAACCATA    2760

GATCTCTCAT CATCTTCCCC CGGGCCCCCT GACTTGTCCA GCCTGCCAAC CACACTAGCC    2820

CACTTGCAAA CTATAGACCT TAGAGACGCC TTTTTCCAAA TCCCCTTACC TAAACAGTTC    2880

CAGCCCTACT TTGCTTTCAC TGTCCCACAG CAGTGTAACT ACGGCCCCGG CACTAGATAC    2940

GCCTGGAAAG TACTACCCCA AGGGTTTAAA AATAGTCCCA CCCTGTTCGA AATGCAGCTG    3000

GCCCATATCC TGCAGCCCAT TCGGCAAGCT TTCCCCCAAT GCACTATTCT TCAGTACATG    3060

GATGACATTC TCCTAGCAAG CCCCTCCCAT GAGGACCTAC TACTACTCTC AGAGGCCACA    3120

ATGGCTTCCC TAATCTCCCA TGGGTTGCCT GTGTCCGAAA ACAAAACCCA GCAAACCCCT    3180

GGAACAATTA AGTTCCTAGG GCAGATAATT TCACCCAATC ACCTCACTTA TGATGCAGTC    3240

CCCACGGTAC CTATACGGTC CCGCTGGGCG CTACCTGAAC TTCAAGCCCT ACTTGGCGAG    3300

ATTCAGTGGG TCTCCAAAGG AACTCCTACC TTACGCCAGC CCCTTCACAG TCTCTACTGT    3360

GCCTTACAAA GGCATACTGA TCCCCGAGAC CAAATATATT TAAATCCTTC TCAAGTTCAA    3420

TCATTAGTGC AGCTGCGGCA GGCCCTGTCA CAGAACTGCC GCAGTAGACT AGTCCAAACC    3480

CTGCCCCTCC TAGGGCTAT TATGCTGACC CTCACTGGCA CCACTACTGT AGTGTTCCAG    3540

TCCAAGGAGC AGTGGCCACT TGTCTGGCTA CATGCCCCCC TACCCACAC TAGCCAGTGC    3600

CCCTGGGGGC AGCTACTTGC CTCAGCTGTG TTATTACTCG ACAAATACAC CTTGCAATCC    3660

TATGGGCTGC TCTGCCAAAC CATACATCAT AACATCTCCA CCCAAACCTT CAACCAATTC    3720

ATTCAAACAT CTGACCACCC CAGTGTTCCT ATCTTACTCC ACCACAGTCA CCGATTCAAA    3780

AATTTAGGTG CCCAAACTGG AGAACTTTGG AACACTTTTC TTAAAACAGC TGCCCCATTG    3840

GCTCCTGTGA AAGCCCTCAT GCCAGTGTTT ACTCTTTCCC CGGTGATTAT AAACACCGCC    3900

CCCTGCCTGT TTTCAGACGG ATCTACCTCC CGGGCAGCCT ATATTCTCTG GACAAGCAA    3960

ATATTGTCAC AAAGATCATT CCCCCTTCCG CCACCGCACA AGTCGGCCCA ACGGGCCGAA    4020

CTTCTCGGAC TTTTGCATGG CCTCTCCAGC GCCCGTTCGT GGCGCTGTCT CAACATATTT    4080

CTAGACTCCA AGTATCTTTA TCATTACCTT CGGACCCTTG CCCTGGGCAC CTTCAAGGC    4140

AGGTCCTCTC AGGCCCCCTT TCAGGCCCTT CTGCCCCGCT TACTATCGCG TAAGGTCGTC    4200

TATTTGCACC ACGTTCGCAG CCATACCAAT CTACCTGATC CCATCTCCAG GCTCAACGCT    4260

CTCACAGATG CCCTACTAAT CACCCCTGTC CTGCAGCTCT CTCCTGCAGA ACTACACAGT    4320

TTCACCCATT GCGGACAGAC GGCCCTCACA TTGCAAGGGG CAACCACAAC TGAGGCTTCC    4380

AATATCCTGC GCTCTTGCCA CGCCTGCCGC GGAGGCAACC CACAACATCA GATGCCTCGG    4440

GGACACATCC GCCGTGGCCT ACTTCCTAAC CACATCTGGC AAGGCGACAT TACCCATTTC    4500

AAATATAAAA ATACGCTGTA TCGCCTTCAT GTATGGGTAG ACACCTTTTC AGGAGCCATC    4560

TCAGCTACCC AAAAGAGAAA AGAAACAAGC TCAGAAGCTA TTTCCTCTTT GCTTCAGGCC    4620

ATTGCCCATC TAGGCAAGCC TAGCTACATA AACACAGACA ACGGCCCTGC CTATATTTCC    4680

CAAGACTTCC TCAATATGTG TACCTCCCTT GCTATTCGCC ATACCACCCA TGTCCCCTAC    4740

AATCCAACCA GCTCAGGACT TGTAGAACGC TCTAATGGCA TTCTTAAAAC CCTATTATAT    4800

AAGTACTTTA CTGACAAACC CGACCTACCC ATGGATAATG CTCTATCCAT AGCCCTATGG    4860

ACAATCAACC ACCTGAATGT GTTAACCAAC TGCCACAAAA CCCGATGGCA GCTTCACCAC    4920

TCCCCCCGAC TCCAGCCGAT CCCAGAGACA CGTTCCCTCA GCAATAAACA AACCCATTGG    4980
```

-continued

```
TATTATTTCA AGCTTCCTGG TCTTAATAGC CGCCAGTGGA AAGGACCACA GGAGGCTCTC    5040

CAAGAAGCTG CCGGCGCTGC TCTCATCCCG GTAAGCGCTA GTTCTGCCCA GTGGATCCCG    5100

TGGAGACTCC TCAAGCGAGC TGCATGCCCA AGACCCGTCG GAGGCCCCGC CGATCCCAAA    5160

GAAAAAGACC TCCAACACCA TGGGTAAGTT TCTCGCCACT TTGATTTTAT TCTTCCAGTT    5220

CTGCCCCCTC ATCTTCGGTG ATTACAGCCC CAGCTGCTGT ACTCTCACAA TTGGAGTCTC    5280

CTCATACCAC TCTAAACCCT GCAATCCTGC CCAGCCAGTT TGTTCGTGGA CCCTCGACCT    5340

GCTGGCCCTT TCAGCAGATC AGGCCCTACA GCCCCCCTGC CCTAACCTAG TAAGTTACTC    5400

CAGCTACCAT GCCACCTATT CCCTATATCT ATTCCCTCAT TGGACTAAGA AGCCAAACCG    5460

AAATGGCGGA GGCTATTATT CAGCCTCTTA TTCAGACCCT TGTTCCTTAA AGTGCCCATA    5520

CCTGGGGTGC CAATCATGGA CCTGCCCCTA TACAGGAGCC GTCTCCAGCC CCTACTGGAA    5580

GTTTCAACAC GATGTCAATT TTACTCAAGA AGTTTCACGC CTCAATATTA ATCTCCATTT    5640

TTCAAAATGC GGTTTTCCCT TCTCCCTTCT AGTCGACGCT CCAGGATATG ACCCCATCTG    5700

GTTCCTTAAT ACCGAACCCA GCCAACTGCC TCCCACCGCC CCTCCTCTAC TCCCCCACTC    5760

TAACCTAGAC CACATCCTCG AGCCCTCTAT ACCATGGAAA TCAAAACTCC TGACCCTTGT    5820

CCAGTTAACC CTACAAAGCA CTAATTATAC TTGCATTGTC TGTATCGATC GTGCCAGCCT    5880

CTCCACTTGG CACGTCCTAT ACTCTCCCAA CGTCTCTGTT CCATCCTCTT CTTCTACCCC    5940

CCTCCTTTAC CCATCGTTAG CGCTTCCAGC CCCCCACCTG ACGTTACCAT TTAACTGGAC    6000

CCACTGCTTT GACCCCAGA TTCAAGCTAT AGTCTCCTCC CCCTGTCATA ACTCCCTCAT     6060

CCTGCCCCCC TTTTCCTTGT CACCTGTTCC CACCCTAGGA TCCCGCTCCC GCCGAGCGGT    6120

ACCGGTGGCG GTCTGGCTTG TCTCCGCCCT GGCCATGGGA GCCGGAGTGG CTGGCGGGAT    6180

TACCGGCTCC ATGTCCCTCG CCTCAGGAAA GAGCCTCCTA CATGAGGTGG ACAAAGATAT    6240

TTCCCAGTTA ACTCAAGCAA TAGTCAAAAA CCACAAAAAT CTACTCAAAA TTGCGCAGTA    6300

TGCTGCCCAG AACAGACGAG GCCTTGATCT CCTGTTCTGG GAGCAAGGAG GATTATGCAA    6360

AGCATTACAA GAACAGTGCC GTTTTCCGAA TATTACCAAT TCCCATGTCC CAATACTACA    6420

AGAAAGACCC CCCCTTGAGA ATCGAGTCCT GACTGGCTGG GGCCTTAACT GGGACCTTGG    6480

CCTCTCACAG TGGGCTCGAG AGGCCTTACA AACTGGAATC ACCCTTGTTG CGCTACTCCT    6540

TCTTGTTATC CTTGCAGGAC CATGCATCCT CCGTCAGCTA CGACACCTCC CCTCGCGCGT    6600

CAGATACCCC CATTACTCTC TTATAAAACC TGAGTCATCC CTGTAAACCA AGCACGCAAT    6660

TATTGCAACC ACATCGCCTC CAGCCTCCCC TGCCAATAAT TAACCTCTCC CATCAAATCC    6720

TCCTTCTCCT GCAGCAACTT CCTCCGTTCA GCCTCCAAGG ACTCCACCTC GCCTTCCAAC    6780

TGTCTAGTAT AGCCATCAAT CCCCAACTCC TGCATTTTTT CTTTCCTAGC ACTATGCTGT    6840

TTCGCCTTCT CAGCCCCTTG TCTCCACTTG CGCTCACGGC GCTCCTGCTC TTCCTGCTTC    6900

CTCCTAGCGA CGTCAGCGGC CTTCTTCTCC GCCCGCCTCC TGCGCCGTGC CTTCTCCTCT    6960

TCCTTCCTTT TCAAATACTC AGCGGTCTGC TTTTCCTCCT CTTTCTCCCG CTCTTTTTTT    7020

CGCTTCCTCT TCTCCTCAGC CCGTCGCTGC CGATCACGAT GCGTTTCCCC GCGAGGTGGC    7080

GCTTTCTCCC CTGGAGGGCC CCGTCGCAGC CGGCCGCGGC TTTCCTCTTC TAAGGATAGC    7140

AAACCGTCAA GCACAGCTTC CTCCTCCTCC TTGTCCTTTA ACTCTTCCTC CAAGGATAAT    7200

AGCCCGTCCA CCAATTCCTC CACCAGCAGG TCCTCCGGGC ATGACACAGG CAAGCATCGA    7260

AACAGCCCTG CAGATACAAA GTTAACCATG CTTATTATCA GCCCACTTCC CAGGGTTTGG    7320
```

```
ACAGAGTCTT CTTTTCGGAT ACCCAGTCTA CGTGTTTGGA GACTGTGTAC AAGGCGACTG      7380

GTGCCCCATC TCTGGGGGAC TATGTTCGGC CCGCCTACAT CGTCACGCCC TACTGGCCAC      7440

CTGTCCAGAG CATCAGATCA CCTGGGACCC CATCGATGGA CGCGTTATCG GCTCAGCTCT      7500

ACAGTTCCTT ATCCCTCGAC TCCCCTCCTT CCCCACCCAG AGAACCTCTA AGACCCTCAA      7560

GGTCCTTACC CCGCCAATCA CTCATACAAC CCCCAACATT CCACCCTCCT TCCTCCAGGC      7620

CATGCGCAAA TACTCCCCCT TCCGAAATGG ATACATGGAA CCCACCCTTG GGCAGCACCT      7680

CCCAACCCTG TCTTTTCCAG ACCCCGGACT CCGGCCCCAA AACCTGTACA CCCTCTGGGG      7740

AGGCTCCGTT GTCTGCATGT ACCTCTACCA GCTTTCCCCC CCCATCACCT GGCCCCTCCT      7800

GCCCCACGTG ATTTTTTGCC ACCCCGGCCA GCTCGGGGCC TTCCTCACCA ATGTTCCCTA      7860

CAAGCGAATA GAAGAACTCC TCTATAAAAT TTCCCTCACC ACAGGGGCCC TAATAATTCT      7920

ACCCGAAGAC TGTTTGCCCA CCACCCTTTT CCAGCCTGCT AGGGCACCCG TCACGCTAAC      7980

AGCCTGGCAA AACGGCCTCC TTCCGTTCCA CTCAACCCTC ACCACTCCAG GCCTTATTTG      8040

GACATTTACC GATGGCACGC CTATGATTTC CGGGCCCTGC CCTAAAGATG GCCAGCCATC      8100

TTTAGTACTA CAGTCCTCCT CCTTTATATT TCACAAATTT CAAACCAAGG CCTACCACCC      8160

CTCATTTCTA CTCTCACACG GCCTCATACA GTACTCTTCC TTTCATAGTT TACATCTCCT      8220

GTTTGAAGAA TACACCAACA TCCCCATTTC TCTACTTTTT AACGAAAAAG AGGCAGATGA      8280

CAATGACCAT GAGCCCCAAA TATCCCCCGG GGGCTTAGAG CCTCCCAGTG AAAAACATTT      8340

CCGAGAAACA GAAGTCTGAA AAGGTCAGGG CCCAGACTAA GGCTCTGACG TCTCCCCCCG      8400

GAGGGCAGCT CAGCACCGGC TCGGGCTAGG CCCTGACGTG TCCCCCTGAA GACAAATCAT      8460

AAGCTCAGAC CTCCGGGAAG CCACCAAGAA CCACCCATTT CCTCCCCATG TTTGTCAAGC      8520

CGTCCTCAGG CGTTGACGAC AACCCCTCAC CTCAAAAAAC TTTTCATGGC ACGCATATGG      8580

CTCAATAAAC TAGCAGGAGT CTATAAAAGC GTGGAGACAG TTCAGGAGGG GGCTCGCATC      8640

TCTCCTTCAC GCGCCCGCCG CCCTACCTGA GGCCGCCATC CACGCCGGTT GAGTCGCGTT      8700

CTGCCGCCTC CCGCCTGTGG TGCCTCCTGA ACTGCGTCCG CCGTCTAGGT AAGTTTAAAG      8760

CTCAGGTCGA GACCGGGCCT TTGTCCGGCG CTCCCTTGGA GCCTACCTAG ACTCAGCCGG      8820

CTCTCCACGC TTTGCCTGAC CCTGCTTGCT CAACTCTACG TCTTTGTTTC GTTTTCTGTT      8880

CTGCGCCGTT ACAGATCGAA AGTTCCACCC CTTTCCCTTT CATTCACGAC TGACTGCCGG      8940

CTTGGCCCAC GGCCAAGTAC CGGCGACTCC GTTGGCTCGG AGCCAGCGAC AGCCCATCCT      9000

ATAGCACTCT CAGGAGAGAA ATTTAGTACA CATAGTTGGA GGTAG                     9045

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:2:

CCAGCGGCCG CGACCTCCAA GACCTCCTG                                         29

(2) INFORMATION FOR SEQ ID NO:3:

(i) SEQUENCE CHARACTERISTICS:
        (A) LENGTH: 29 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:3:

AAAGCGGCCG CCCGATAGCC TTGTTCTCA                                            29

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:4:

TTTGCGGCCG CAACCCAGCA AACCCCTGG                                            29

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:5:

TTAGCGGCCG CGGCGCTGTC TCAACATAT                                            29

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:6:

AAAGCGGCCG CCGTTCCCTC AGCAATAAA                                            29

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:7:

AAAGCGGCCG CGAAGGACTG TCATGTCTG                                            29

(2) INFORMATION FOR SEQ ID NO:8:

(i) SEQUENCE CHARACTERISTICS:

```
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:8:

ACTGCGGCCG CCCAGGGGTT TGCTGGGTT                                            29

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:9:

TTAGCGGCCG CATATGTTGA GACAGCGCC                                            29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:10:

AAAGCGGCCG CAATACCAAT GGGTTTGTT                                            29

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:11:

AATGCGGCCG CCTCGAGGAT GTGGTCTAG                                            29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:12:

AAAGCGGCCG CACTCAGGTT TTATAAGAG                                            29

(2) INFORMATION FOR SEQ ID NO:13:
```

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:13:

ATAGCGGCCG CCCCACTTCC CAGGGTTTG                                29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:14:

TATGCGGCCG CAGGAAGAGT ACTGTATGA                                29

(2) INFORMATION FOR SEQ ID NO:15:

(i) SEQUENCE CHARACTERISTICS:
        (A) LENGTH: 3777 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 139..2151

(xi) SEQUENCE DESCRIPTION: SEQ ID NO:15:

CACGCGTCCG GCCGCCGAAG GGGACTGTTT GCTCCTACGG GCTGTAGATG GAGCTGTCCG    60

GCCCCGGAGA GGGGGAAGGC GCCTGGAAAA CGTTCTTCTT CTCCCTGGCC GACCCGAGCG   120

GGGAACAGCA CTCCCAGG ATG CAG TTT GTG TCA ACA CGG CCG CAG CCT CAG     171
                   Met Gln Phe Val Ser Thr Arg Pro Gln Pro Gln
                     1               5                  10

CAG CTG GGC ATC CAG GGC CTG GGG CTG GAC AGC GGG AGC TGG AGC TGG     219
Gln Leu Gly Ile Gln Gly Leu Gly Leu Asp Ser Gly Ser Trp Ser Trp
             15                  20                  25

GCC CAG GCT CTG CCC CCG GAG CAG GTC TGC CAC CAG GAG CCG GCG CTG     267
Ala Gln Ala Leu Pro Pro Glu Gln Val Cys His Gln Glu Pro Ala Leu
         30                  35                  40

CGC GGG GAA ATG GCC GAG GGA ATG CCG CCC ATG CAG GCT CAA GAA TGG     315
Arg Gly Glu Met Ala Glu Gly Met Pro Pro Met Gln Ala Gln Glu Trp
     45                  50                  55

GAC ATG GAC GCC CGG CGG CCA ATG CCT TTT CAG TTC CCA CCC TTT CCA     363
Asp Met Asp Ala Arg Arg Pro Met Pro Phe Gln Phe Pro Pro Phe Pro
 60                  65                  70                  75

GAT AGG GCA CCT GTC TTC CCC GAC CGC ATG ATG CGA GAG CCC CAG TTG     411
Asp Arg Ala Pro Val Phe Pro Asp Arg Met Met Arg Glu Pro Gln Leu
                 80                  85                  90

CCC ACA GCA GAG ATC TCA CTC TGG ACT GTG GTG GCT GCC ATT CAG GCT     459
Pro Thr Ala Glu Ile Ser Leu Trp Thr Val Val Ala Ala Ile Gln Ala
             95                 100                 105

GTG GAG AGG AAG GTG GAT GCC CAG GCC AGC CAG CTG CTG AAC CTG GAG     507

-continued

```
Val Glu Arg Lys Val Asp Ala Gln Ala Ser Gln Leu Leu Asn Leu Glu
            110                 115                 120

GGG CGC ACG GGG ACA GCC GAG AAG AAG CTG GCC GAC TGT GAA AAG ACG      555
Gly Arg Thr Gly Thr Ala Glu Lys Lys Leu Ala Asp Cys Glu Lys Thr
        125                 130                 135

GCC GTG GAA TTT GGG AAC CAC ATG GAG AGC AAG TGG GCC GTG CTG GGG      603
Ala Val Glu Phe Gly Asn His Met Glu Ser Lys Trp Ala Val Leu Gly
140                 145                 150                 155

ACC CTG CTG CAG GAG TAC GGG CTG CTG CAG AGG CGG CTG GAG AAC TTG      651
Thr Leu Leu Gln Glu Tyr Gly Leu Leu Gln Arg Arg Leu Glu Asn Leu
                160                 165                 170

GAG AAC TTG CTG CGC AAC AGG AAC TTC TGG GTC CTG CGG CTG CCC CCG      699
Glu Asn Leu Leu Arg Asn Arg Asn Phe Trp Val Leu Arg Leu Pro Pro
            175                 180                 185

GGC AGC AAG GGG GAG GCC CCC AAG GTT CCA GTG ACT TTT GTC GAC ATT      747
Gly Ser Lys Gly Glu Ala Pro Lys Val Pro Val Thr Phe Val Asp Ile
        190                 195                 200

GCT GTG TAC TTC TCC GAA GAC GAG TGG AAG AAC TTG GAC GAA TGG CAG      795
Ala Val Tyr Phe Ser Glu Asp Glu Trp Lys Asn Leu Asp Glu Trp Gln
205                 210                 215

AAG GAG CTT TAT AAC AAC CTT GTT AAG GAG AAC TAC AAA ACC CTC ATG      843
Lys Glu Leu Tyr Asn Asn Leu Val Lys Glu Asn Tyr Lys Thr Leu Met
220                 225                 230                 235

TCC CTG GAC GCG GAG GGC TCA GTC CCC AAG CCA GAT GCT CCA GTC CAG      891
Ser Leu Asp Ala Glu Gly Ser Val Pro Lys Pro Asp Ala Pro Val Gln
                240                 245                 250

GCT GAG CCC AGG GAA GAA CCT TGT GTG TGG GAG CAG CGC CAC CCC GAA      939
Ala Glu Pro Arg Glu Glu Pro Cys Val Trp Glu Gln Arg His Pro Glu
            255                 260                 265

GAG AGA GAA ATC CCA ATG GAT CCC GAA GCA GGA GCA GAG CCC CTG GTG      987
Glu Arg Glu Ile Pro Met Asp Pro Glu Ala Gly Ala Glu Pro Leu Val
        270                 275                 280

CCT GCG CAG GAT GCG TCC TCC CAG GTG AAG CGT GAG GAC ACC CTG TGT     1035
Pro Ala Gln Asp Ala Ser Ser Gln Val Lys Arg Glu Asp Thr Leu Cys
285                 290                 295

GTC CGG GGT CAG CGG GGC CTG GAG GAA AGA GCC ATC CCT ACG GAA TCC     1083
Val Arg Gly Gln Arg Gly Leu Glu Glu Arg Ala Ile Pro Thr Glu Ser
300                 305                 310                 315

ATT ACC GAC TCC CCA ATT TCT GCC CAG GAC CTC TTG TCC CGG ATT AAA     1131
Ile Thr Asp Ser Pro Ile Ser Ala Gln Asp Leu Leu Ser Arg Ile Lys
                320                 325                 330

CAG GAG GAG CAT CAG TGC GTG TGG GAT CAG CAG GAT TTG GCA GAC AGA     1179
Gln Glu Glu His Gln Cys Val Trp Asp Gln Gln Asp Leu Ala Asp Arg
            335                 340                 345

GAT ATT CCC ACG GAT CCC AAT TCA GAG TCT CTC ATC TCA GCA CAT GAC     1227
Asp Ile Pro Thr Asp Pro Asn Ser Glu Ser Leu Ile Ser Ala His Asp
        350                 355                 360

ATT TTG TCA TGG ATC AAG CAG GAG GAG CAG CCA TAC CCA TGG GGA CCA     1275
Ile Leu Ser Trp Ile Lys Gln Glu Glu Gln Pro Tyr Pro Trp Gly Pro
365                 370                 375

CGC GAC TCA ATG GAC GGA GAG CTT GGA TTA GAC TCT GGC CCT AGT GAC     1323
Arg Asp Ser Met Asp Gly Glu Leu Gly Leu Asp Ser Gly Pro Ser Asp
380                 385                 390                 395

AGC CTG CTG ATG GTG AAG AAC CCA CCC CCG GCC CCG CCA CAG CCC CAG     1371
Ser Leu Leu Met Val Lys Asn Pro Pro Pro Ala Pro Pro Gln Pro Gln
                400                 405                 410

CCC CAG CGC CAG CCA CCG CAG CCG CAG CTG CAG TCG CAG CCC CAG CCC     1419
Pro Gln Arg Gln Pro Pro Gln Pro Gln Leu Gln Ser Gln Pro Gln Pro
            415                 420                 425
```

```
CAG AGC CTG CCC CCC ATC GCG GTG GCC GAG AAC CCG GGC GGC CCC CCG    1467
Gln Ser Leu Pro Pro Ile Ala Val Ala Glu Asn Pro Gly Gly Pro Pro
        430                 435                 440

AGC CGA GGG CTG CTG GAC GAC GGT TTC CAG GTG CTG CCC GGG GAG CGT    1515
Ser Arg Gly Leu Leu Asp Asp Gly Phe Gln Val Leu Pro Gly Glu Arg
        445                 450                 455

GGC TCC GGC GAG GCG CCG CCG GGT GGG GAC CGC AGC ACC GGG GGC GGC    1563
Gly Ser Gly Glu Ala Pro Pro Gly Gly Asp Arg Ser Thr Gly Gly Gly
460                 465                 470                 475

GGG GGC GAT GGG GGC GGT GGG GGC GGC GCG GAG GCG GGG ACG GGG        1611
Gly Gly Asp Gly Gly Gly Gly Gly Gly Ala Glu Ala Gly Thr Gly
                480                 485                 490

GCA GGC GGC GGC TGT GGC AGC TGC TGC CCT GGC GGG CTG CGG CGG AGC    1659
Ala Gly Gly Gly Cys Gly Ser Cys Cys Pro Gly Gly Leu Arg Arg Ser
                495                 500                 505

CTC CTC CTG CAC GGC GCC CGC AGC AAG CCC TAC TCG TGC CCC GAG TGC    1707
Leu Leu Leu His Gly Ala Arg Ser Lys Pro Tyr Ser Cys Pro Glu Cys
        510                 515                 520

GGC AAG AGC TTC GGC GTG CGC AAG AGC CTC ATC ATC CAC CAC CGC AGC    1755
Gly Lys Ser Phe Gly Val Arg Lys Ser Leu Ile Ile His His Arg Ser
        525                 530                 535

CAC ACC AAG GAG CGG CCC TAC GAG TGC GCT GAG TGC GAG AAG AGC TTC    1803
His Thr Lys Glu Arg Pro Tyr Glu Cys Ala Glu Cys Glu Lys Ser Phe
540                 545                 550                 555

AAC TGC CAC TCG GGC CTC ATC CGC CAC CAG ATG ACG CAC CGC GGC GAG    1851
Asn Cys His Ser Gly Leu Ile Arg His Gln Met Thr His Arg Gly Glu
                560                 565                 570

CGG CCC TAC AAG TGC TCG GAG TGC GAG AAG ACC TAC AGC CGT AAG GAG    1899
Arg Pro Tyr Lys Cys Ser Glu Cys Glu Lys Thr Tyr Ser Arg Lys Glu
                575                 580                 585

CAC CTG CAG AAC CAC CAG CGG CTG CAC ACG GGC GAG CGG CCT TTC CAA    1947
His Leu Gln Asn His Gln Arg Leu His Thr Gly Glu Arg Pro Phe Gln
        590                 595                 600

TGT GCA CTG TGC GGC AAG AGC TTC ATC CGC AAG CAG AAC CTG CTC AAG    1995
Cys Ala Leu Cys Gly Lys Ser Phe Ile Arg Lys Gln Asn Leu Leu Lys
605                 610                 615

CAC CAG CGC ATC CAC ACG GGC GAG CGC CCC TAC ACG TGC GGC GAG TGC    2043
His Gln Arg Ile His Thr Gly Glu Arg Pro Tyr Thr Cys Gly Glu Cys
620                 625                 630                 635

GGC AAG AGC TTC CGC TAC AAG GAG TCG CTC AAG GAC CAC CTG CGC GTG    2091
Gly Lys Ser Phe Arg Tyr Lys Glu Ser Leu Lys Asp His Leu Arg Val
                640                 645                 650

CAC AGC GGC GGC CCG GGC CCC GGC GCC CCA CGG CAG CTC CCG CCG CCT    2139
His Ser Gly Gly Pro Gly Pro Gly Ala Pro Arg Gln Leu Pro Pro Pro
                655                 660                 665

CCT GAG CGA GAC TAGGGCTGGG CTGGGGAGG GCAGGGCCGG ACGGAGTGGA         2191
Pro Glu Arg Asp
        670

TCGGGGCGG CCTGAGCACC AACCACCTTG CCGGGTGTCC TCAGCCACCG TCTGGAAATC   2251

GGCAACAGGC ATTGCACTCC GGTTGGGGGT CCCCCAGGGT GGGGCAGGGA TCCCCCAGAT  2311

CTGTCTGGTC TGAATGGACG CCCAGCTCAT CTAGGGTGGA CCCAGCTGCT GGGGAAGAGC  2371

CAGGGGGACC GCGAGGAGCC GAGCGTCCTC GGGCACCGCC CTCACACCTC CTCGAGTGCC  2431

CTGGGACCAC TGGGCCACAG ATGGTCATCA GGGGAAGCCA CCAGGGAGTC CCGAAGCCCT  2491

TCTGAGATCA GGAAATCAGG TCCCAAGGTT AGGAGACGCC CTGAAAAAAA GTGAAGGCCG  2551

AGGGATGTGC TAAGGGTAAC ACCTTCATGA TGACAACACT GCCTCGCGTT TCAATAGCGC  2611

TTTATACTTT TTTAAGTGTT TTCTATCCGT TATCCATTTC ACCCTTGGCC TATCCCTCTC  2671
```

```
AGATAGGTGG GGTAGGATTT TCCTGGTGAC CGAGTAAAGT GAGAGGCAGG TGAGACGGTT      2731

CACCCAATCA CACGGGAAGG GGCGCGCGCT GCCCAACCGC GCTCTCCGCC TACCTCGCTG      2791

CTCGGGAAGC TGCTGGCCTG GCCCTCCTGG TCTCTCTTCC TTTCTGGTCT CTCTTCCTTT      2851

CCTTGCTCTC ACCCACGGAT AAAACCAGAA GCGACAGGAG GCCAGCTCCT GGGGTTCCTG      2911

GGACCGGGAA CAGATTGGCT ACGGAACGCC CCAGGTTGTA CATTCAGAGG GCTCTTTCTC      2971

CATGGGAGCT CCTGGTGCCG CCTTCGGCCC CAGCCTGTCC CCAGCCCCTC AATCTGGTGC      3031

AGCAGCATCT TGTCACTGCA CAACAGTGGC CTGGTCCCCC ACAGGCAGTT AGGGCCCCAG      3091

GTCAGACCTC ACCATGATGA TTTGTTCCAG TTCTCCCAGG GCAGAGGGGC GAGGGAGAGG      3151

CTTTTGCTGT GAGAGTAGCC GTCACGTGTC TCTTCCCAGC AGCGCCGGGC AAGTGGGTGC      3211

TAGAGTCTGA GCCTCAGGCT CTCCTGCCCT GGGCCTCCCA ATTGGTGCTA TCTGTTACTG      3271

CCCGTGCTCA CGGACATGGA TACAGACCCT GCTGTGCTCC ACACCCTGCA GGCGCCTCGG      3331

GAAGCGCCCA AAGGATTCCC CTTCACGTTG GTGCACCTGC TCCATAGCTC CGGGCGCTGC      3391

GTCCCGAGGG GCCACAGTCT CCATTTCAGC GTCTTGCATG GCCTGGCACC GGGTGGGGTG      3451

GTATGCCCCC TTGTTTGTGT CAAAAATGAC TTTCCCTGCC CTTGCCGTGG GTCCGGCGTT      3511

CCTCCCAGCC GGGATCACAG TGGGCAGCCG GCACCCGGCA CCACTTTGGC GAGCGTCCTG      3571

CTTCCGCCCT CGCCCTCATC TACGCTGCTC CGCTTTCCTC AGACCCCTTT TTGCCGTGCA      3631

AAGGAATTCT TGACATTAAA TAAAAGGTAT CCAGATTGCA GACTGCATGT TCACAGAGCT      3691

GGGGGTTCTC CAGCTTGCCT ACAGTAAAGC CTCAATGAAC TGGAAAAAAA AAAAAAAAAA      3751

AAAAAAAAAA AAAAAAAAAA AAAAA                                           3777

(2) INFORMATION FOR SEQ ID NO:16:

(i) SEQUENCE CHARACTERISTICS:
        (A) LENGTH: 671 amino acids
        (B) TYPE: amino acid
        (D) TOPOLOGY: linear (ii) MOLECULE TYPE: protein (xi) SEQUENCE DESCRIPTION: SEQ ID NO:16:

Met Gln Phe Val Ser Thr Arg Pro Gln Pro Gln Leu Gly Ile Gln
  1               5                  10                  15

Gly Leu Gly Leu Asp Ser Gly Ser Trp Ser Trp Ala Gln Ala Leu Pro
                 20                  25                  30

Pro Glu Gln Val Cys His Gln Glu Pro Ala Leu Arg Gly Glu Met Ala
             35                  40                  45

Glu Gly Met Pro Pro Met Gln Ala Gln Glu Trp Asp Met Asp Ala Arg
     50                  55                  60

Arg Pro Met Pro Phe Gln Phe Pro Pro Phe Pro Asp Arg Ala Pro Val
 65                  70                  75                  80

Phe Pro Asp Arg Met Met Arg Glu Pro Gln Leu Pro Thr Ala Glu Ile
                 85                  90                  95

Ser Leu Trp Thr Val Ala Ala Ile Gln Ala Val Glu Arg Lys Val
                100                 105                 110

Asp Ala Gln Ala Ser Gln Leu Leu Asn Leu Glu Gly Arg Thr Gly Thr
             115                 120                 125

Ala Glu Lys Lys Leu Ala Asp Cys Glu Lys Thr Ala Val Glu Phe Gly
     130                 135                 140

Asn His Met Glu Ser Lys Trp Ala Val Leu Gly Thr Leu Leu Gln Glu
```

-continued

```
145                 150                 155                 160

Tyr Gly Leu Leu Gln Arg Arg Leu Glu Asn Leu Glu Asn Leu Leu Arg
                165                 170                 175

Asn Arg Asn Phe Trp Val Leu Arg Leu Pro Pro Gly Ser Lys Gly Glu
                180                 185                 190

Ala Pro Lys Val Pro Val Thr Phe Val Asp Ile Ala Val Tyr Phe Ser
                195                 200                 205

Glu Asp Glu Trp Lys Asn Leu Asp Glu Trp Gln Lys Glu Leu Tyr Asn
            210                 215                 220

Asn Leu Val Lys Glu Asn Tyr Lys Thr Leu Met Ser Leu Asp Ala Glu
225                 230                 235                 240

Gly Ser Val Pro Lys Pro Asp Ala Pro Val Gln Ala Glu Pro Arg Glu
                245                 250                 255

Glu Pro Cys Val Trp Glu Gln Arg His Pro Glu Glu Arg Glu Ile Pro
                260                 265                 270

Met Asp Pro Glu Ala Gly Ala Glu Pro Leu Val Pro Ala Gln Asp Ala
            275                 280                 285

Ser Ser Gln Val Lys Arg Glu Asp Thr Leu Cys Val Arg Gly Gln Arg
        290                 295                 300

Gly Leu Glu Glu Arg Ala Ile Pro Thr Glu Ser Ile Thr Asp Ser Pro
305                 310                 315                 320

Ile Ser Ala Gln Asp Leu Leu Ser Arg Ile Lys Gln Glu Glu His Gln
                325                 330                 335

Cys Val Trp Asp Gln Gln Asp Leu Ala Asp Arg Asp Ile Pro Thr Asp
                340                 345                 350

Pro Asn Ser Glu Ser Leu Ile Ser Ala His Asp Ile Leu Ser Trp Ile
            355                 360                 365

Lys Gln Glu Glu Gln Pro Tyr Pro Trp Gly Pro Arg Asp Ser Met Asp
        370                 375                 380

Gly Glu Leu Gly Leu Asp Ser Gly Pro Ser Asp Ser Leu Leu Met Val
385                 390                 395                 400

Lys Asn Pro Pro Pro Ala Pro Pro Gln Pro Gln Pro Gln Arg Gln Pro
                405                 410                 415

Pro Gln Pro Gln Leu Gln Ser Gln Pro Gln Pro Gln Ser Leu Pro Pro
            420                 425                 430

Ile Ala Val Ala Glu Asn Pro Gly Gly Pro Pro Ser Arg Gly Leu Leu
        435                 440                 445

Asp Asp Gly Phe Gln Val Leu Pro Gly Glu Arg Gly Ser Gly Glu Ala
    450                 455                 460

Pro Pro Gly Gly Asp Arg Ser Thr Gly Gly Gly Gly Asp Gly Gly
465                 470                 475                 480

Gly Gly Gly Gly Ala Glu Ala Gly Thr Gly Ala Gly Gly Cys
                485                 490                 495

Gly Ser Cys Cys Pro Gly Gly Leu Arg Arg Ser Leu Leu His Gly
                500                 505                 510

Ala Arg Ser Lys Pro Tyr Ser Cys Pro Glu Cys Gly Lys Ser Phe Gly
            515                 520                 525

Val Arg Lys Ser Leu Ile Ile His His Arg Ser His Thr Lys Glu Arg
        530                 535                 540

Pro Tyr Glu Cys Ala Glu Cys Glu Lys Ser Phe Asn Cys His Ser Gly
545                 550                 555                 560

Leu Ile Arg His Gln Met Thr His Arg Gly Glu Arg Pro Tyr Lys Cys
                565                 570                 575
```

```
Ser Glu Cys Glu Lys Thr Tyr Ser Arg Lys Glu His Leu Gln Asn His
            580                 585                 590

Gln Arg Leu His Thr Gly Glu Arg Pro Phe Gln Cys Ala Leu Cys Gly
            595                 600                 605

Lys Ser Phe Ile Arg Lys Gln Asn Leu Leu Lys His Gln Arg Ile His
            610                 615                 620

Thr Gly Glu Arg Pro Tyr Thr Cys Gly Glu Cys Gly Lys Ser Phe Arg
625                 630                 635                 640

Tyr Lys Glu Ser Leu Lys Asp His Leu Arg Val His Ser Gly Gly Pro
                    645                 650                 655

Gly Pro Gly Ala Pro Arg Gln Leu Pro Pro Pro Glu Arg Asp
            660                 665                 670

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:17:

GATCTAAGTT CCACCCCTTT CCCTTTCATT CG                              32

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:18:

GATCCGAATG AAAGGGAAAG GGGTGGAACT TA                              32

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:19:

CCTGAGGTAA TTATAACCCG                                            20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

```
     (ii) MOLECULE TYPE: other nucleic acid
          (A) DESCRIPTION: /desc = "synthetic DNA"

(xi) SEQUENCE DESCRIPTION: SEQ ID NO:20:

CGCTGATATC GATCGCGCGC                                           20
```

DNA MOLECULE RELATING TO SUPPRESSION OF GENE EXPRESSION AND NOVEL PROTEIN

This is a division of U.S. patent application Ser. No. 08/933,803 filed Sep. 19, 1997, pending, the entire disclosure of which is hereby incorporated by reference, that application is a continuation in part of U.S. patent application Ser. No. 08/913,665 filed Sep. 19, 1997, pending, which is the United States national phase filing of International Application No. PCT/JP96/00719, filed Mar. 19, 1996.

TECHNICAL FIELD

The present invention relates to DNA molecules and novel proteins associated with the repression of gene expression. In particular, the present invention relates to a DNA molecule having a gene expression repressing function, derived from human T-cell leukemia virus type I, and a plasmid including the DNA molecule. The present invention also relates to a protein which binds to a transcriptional repressive region existing in the U5 region of human T-cell leukemia virus type I gene LTR; a structural gene for the protein; an expression vector including the gene; a transformant into which the expression vector is introduced; and a process, using the above transformant, for producing a protein which binds to a transcriptional repressive region existing in the U5 region of human T-cell leukemia virus type I gene LTR. Furthermore, the present invention relates to an antiviral agent containing the protein, and a method for detecting cancer that utilizes the expression of the protein as an indicator.

BACKGROUND ART

In 1980, Human T-cell leukemia virus type I (HTLV-1) became the first retrovirus discovered in humans. It has been revealed that infection by this virus causes diseases such as adult T-cell leukemia (ATL), HTLV-I associated myelopathy (HAM), and tropical spastic paraparesis (TSP), and that the symptoms of such diseases develop after a long period of time in the body, with an average latency of about 40 to 50 years after the infection with the virus. However, little is known about the mechanisms of its latent infection and onset.

The gene of HTLV-I includes a tax/rex region in addition to three regions which are common to animal retroviruses, i.e., a gag region, a pol region, and an env region. The tax/rex region, which is located down-stream of env, is considered to have an important role in the expression of viral gene and the onset of ATL. The mRNA of tax/rex results after double splicings from a primary transcript of the HTLV-I gene, and includes two overlapping open reading frames. From one open reading frame is translated a 40 kilodalton protein called Tax, which acts on the LTR of the virus itself as well as promoters of various genes in cells to activate transcription. From the other open reading frame is translated a 27 kilodalton protein called Rex, which controls the processing of the viral RNA occurring within the nucleus after transcription, and positively acts on the transport to the cytoplasm of unspliced mRNA.

From a different start codon within the same open reading frame as that of the Rex protein, a 21kD protein called p21X is translated. The inventors revealed that p21X is translated from the p21X mRNA which lacks the second exon through single splicing from the HTLV-I gene (Orita et al. FEBS Lett., 295, 127–134 (1991)). However, the functions of the protein are unknown. The inventors further discovered that the p21X mRNA is expressed by a mutant provirus having a deletion in a broad region encompassing the gag, pol, and env regions in a HTLV-I infected cell line (Orita et al. Nucleic Acids, Res., 21, 3799–3807 (1993)). Moreover, the inventors discovered that the p21X mRNA is also expressed by the above-mentioned mutant provirus in peripheral blood lymphocytes of patients infected with HTLV-I. On the other hand, it is known that the expression of mRNA for the tax/rex region from a complete provirus is rarely observed in the peripheral blood of patients infected with HTLV-I, and is detectable in vivo only by the RT-PCR method, which is an ultra-sensitive detection method. However, once peripheral blood lymphocytes of patients infected with HTLV-I are transferred to a culture system in vitro, its expression is known to become high enough to be easily detected (Kiyokawa et al., Proc. Natl. Acad. Sci. USA., 82, 8359–8363 (1985)). Moreover, the expression of the p21X mRNA has also been found to be on the same level before and after the culture of the aforementioned peripheral blood lymphocytes of patients infected with HTLV-I (Orita et al., J. Gen. Virol., 73, 2283–2289 (1992)). Therefore, it was considered that, in vivo, the p21X mRNA is expressed without being repressed, whereas the expression of the mRNA for tax/rex is repressed.

It is considered that HTLV-I and human immunodeficiency virus (HIV), which is a kind of RNA virus, delays splicing reactions by making the splicing signal within a DNA sequence a non-optimal one, thereby providing time for the Rex protein of HTLV-I or the Rev protein of HIV to repress splicing reactions (Chang, D. D. and Sharp. P. A., Science, 249, 614–615 (1990)). It is considered that sufficient amounts of the Rex protein and the Rev protein need to be expressed and accumulated within the nucleus in order to be polymerized, before their functions can be exhibited to promote the repression of the splicing of the viral mRNA having RXE (Rex responsible element) or RRE (Rev responsible element) and the transport to the cytoplasm, thereby triggering the replication of the viruses (expression of the structural proteins) (Inoue et al., Proc. Natl. Acad. Sci. USA., 84, 3653–3657 (1987); Hidaka et al., EMBO J., 7, 519–523 (1988); Seiki et al. Proc. Natl. Acad. Sci. USA., 85, 7124–7128(1988); and Hanly et al. Genes Dev., 3, 1534–1544(1989)).

The above indicates that at least two regulatory factors, i.e., Tax and Rex proteins, are translated from the pX region characteristic of HTLV-I, and that these factors are necessary for the replication of HTLV-I. Tax is a transcription activation factor which acts on the LTR (long terminal repeat) and also activates various cellular genes. Tax also has an ability to transform certain types of cultured cells. Thus, the possibility of Tax being involved in the oncogenesis of a cell by HTLV-I is suggested.

The expression of the HTLV-I gene is known to be very low in periods of inapparent infection and to be low even after the onset of ATL. Therefore, in order to elucidate the mechanism of latent infection of HTLV-I, it is considered important to study the expression repression mechanism of the viral gene. It is known that the expression control of the HTLV-I gene is performed mainly on the LTR of HTLV-1. The LTR region is subdivided into three regions called U3, R, and U5. The U3 region includes a sequence on which Tax acts, as well as sequences acted upon by CREB, ETS, AP1, etc., which are cellular transcription activation factors. The R region is known to include a sequence to which YB-1 binds to activate transcription (Kashanchi et al. J. Virol., 68(1): 561–565 (1994)). Moreover, the R and U5 regions include a region which functions repressively with respect to the HTLV-I gene expression on the transcription level or post-transcriptionally (Xu et al., Mol. Cell. Biol., 14(8): 5371–5383 (1994); and Seiki et al., Virology, 176: 81–86 (1990)). Furthermore, the inventors recently discovered a novel transcriptional repressive sequence (U5 repressive element; U5RE), and reported the existence of three proteins of 110 kDa, 80 kDa, and 70 kDa which specifically bind to U5RE (Okumura et al. FEBS Let., 356: 94–100 (1994)).

DISCLOSURE OF THE INVENTION

In order to elucidate the gene expression repression mechanism of human T-cell leukemia virus type I, the inventors conducted studies on gene sequences and proteins associated with expression repression.

First, the inventors predicted that a region which represses the expression of the viral gene exists in a region which is missing in a mutant provirus of human T-cell leukemia virus type I (HTLV-I) that is expressing p21X mRNA but exists in the genome of a complete provirus. Accordingly, the inventors incorporated a portion of a DNA sequence of the genome of the virus into a plasmid and conducted studies using an assay system that utilized the expression of the CAT gene as an indicator. As a result, the inventors discovered two gene expression repressive regions in the pol region.

Therefore, according to one aspect of the present invention, there is provided a DNA molecule having a gene expression repressing function derived from human T-cell leukemia virus type I, the DNA molecule being in a region which is missing in a mutant provirus that is expressing p21X mRNA but exists in the genome of a complete provirus; and a plasmid including the DNA molecule.

A DNA molecule having a gene expression repressing function according to the present invention includes a DNA sequence of at least 400 contiguous nucleotides included in a DNA sequence from C at position 2268 to T at position 4080 of SEQ ID NO:1 in the Sequence Listing, or a DNA sequence having homology of about 59% or more with the DNA sequence.

In a preferred embodiment, the DNA molecule is a DNA sequence of at least 400 contiguous nucleotides included in a DNA sequence from C at position 2268 to T at position 4080 of SEQ ID NO:1 in the Sequence Listing, or a DNA sequence having homology of about 59% or more with the DNA sequence.

In a preferred embodiment, the DNA molecule includes a DNA sequence from C at position 2268 to G at position 3182 of SEQ ID NO:1 in the Sequence Listing, or a DNA sequence having homology of about 59% or more with the DNA sequence.

In a preferred embodiment, the DNA molecule includes a DNA sequence from A at position 3368 to A at position 3780 of SEQ ID NO:1 in the Sequence Listing, or a DNA sequence having homology of about 59% or more with the DNA sequence.

In a preferred embodiment, the DNA molecule includes a DNA sequence from A at position 3165 to T at position 4080 of SEQ ID NO:1 in the Sequence Listing, or a DNA sequence having homology of about 59% or more with the DNA sequence.

A plasmid according to the present invention includes a promotor sequence having activity within a host cell, one of the above-described DNA molecules, and a RRE or RXE sequence.

In a preferred embodiment, the plasmid further includes a therapeutic gene sequence.

In a preferred embodiment, the plasmid includes a promoter sequence which enhances the expression efficiency in a virus-infected cell.

In a preferred embodiment, the promoter in the plasmid is LTR.

In a preferred embodiment, the therapeutic gene sequence in the plasmid is a gene sequence which can be toxic to the host cell or a gene sequence capable of preventing virus replication.

A DNA molecule according to the present invention can be used for gene expression repression or the treatment of viral infectious diseases.

In a preferred embodiment, the viral infectious diseases are human T-cell leukemia and HIV infectious diseases, in particular AIDS.

The inventors further conducted various studies on proteins that specifically bind to U5RE, and as a result, isolated a novel cDNA encoding one of the proteins. The inventors allowed this gene to be expressed by using E. coli and found that the resultant product is a protein including a Kruppel-type zinc finger domain of a DNA binding protein and a domain common to Kruppel-type transcriptional repressive factors considered to be involved in transcription repression. Furthermore, the inventors found that the protein binds to U5RE and is involved in transcription repression; the inventors named the protein TRP-1 (Transcriptional repressive Protein-1), thus accomplishing the present invention.

Therefore, according to another aspect of the invention, there is provided a protein, distinct from that of the prior art, that specifically binds to U5RE existing in the U5 region of human T-cell leukemia virus type I gene LTR. In particular, there is provided a protein including a domain common to Kruppel-type transcriptional repressive factors and five Kruppel-type zinc finger domains. According to still another aspect of the invention, there is provided a structural gene for the protein; an expression vector including the gene; a transformant into which the expression vector is introduced; and a process, using the transformant, for producing a protein which binds to a transcriptional repressive region existing in the U5 region of human T-cell leukemia virus type I gene LTR.

A protein (TRP-1) which binds to a transcriptional repressive region existing in the U5 region of human T-cell leukemia virus type I gene LTR according to the present invention includes a domain common to Kruppel-type transcriptional repressive factors and five Kruppel-type zinc finger domains.

In a preferred embodiment, the domain common to Kruppel-type transcriptional repressive factors included in the protein is an amino acid sequence from Val at position 196 to Trp at position 261 of SEQ ID NO:15 in the Sequence Listing, or a similar sequence thereto, and the five Kruppel-type zinc finger domains included in the protein is an amino acid sequence from Tyr at position 518 to Gly at position 657 of SEQ ID NO:15 in the Sequence Listing, or a similar sequence thereto.

In a preferred embodiment, the protein further includes an amino acid sequence from Leu at position 154 to Leu at position 185 of SEQ ID NO:15 in the Sequence Listing, an amino acid sequence from Pro at position 403 to Pro at position 443 of SEQ ID NO:15 in the Sequence Listing, and an amino acid sequence from Arg at position 470 to Gly at position 503 of SEQ ID NO:15 in the Sequence Listing, or sequences similar to such amino acid sequences.

In a preferred embodiment, the protein includes an amino acid sequence from Met at position 1 to Asp at position 671 of SEQ ID NO:15 in the Sequence Listing, or a similar sequence thereto.

A DNA molecule according to the present invention encodes one of the above-described proteins.

In a preferred embodiment, the DNA molecule includes a base sequence from G at position 724 to G at position 921 of SEQ ID NO:15 in the Sequence Listing, and a base sequence from T at position 1690 to C at position 2109 of SEQ ID NO:15 in the Sequence Listing.

In a preferred embodiment, the DNA molecule further includes a base sequence from C at position 598 to G at position 693 of SEQ ID NO:15 in the Sequence Listing, a base sequence from C at position 1345 to G at position 1467 of SEQ ID NO:15 in the Sequence Listing, and a base sequence from C at position 1546 to G at position 1647 of SEQ ID NO:15 in the Sequence Listing.

In a preferred embodiment, the DNA molecule includes a base sequence from A at position 139 to C at position 2151 of SEQ ID NO:15 in the Sequence Listing.

In a preferred embodiment, the DNA molecule includes a base sequence from C at position 1 to A at position 3777 of SEQ ID NO:15 in the Sequence Listing.

An expression vector according to the present invention includes one of the above-described DNA molecules.

A transformant according to the present invention is obtainable by introducing the expression vector into a host.

In a preferred embodiment, the host is *E. coli*.

A process for producing a protein which binds to a transcriptional repressive region existing in the U5 region of human T-cell leukemia virus type I gene LTR according to the present invention includes the steps of culturing the above-described transformant and recovering the produced protein from the culture medium.

The present invention also provides an antiviral agent containing the protein as an effective ingredient. The antiviral agent according to the present invention is effective against HTLV-I as well as human immunodeficiency viruses, and cytomegaloviruses.

The present invention also provides a method for detecting cancer. The method according to the present invention utilizes the expression of the protein as an indicator.

BRIEF DESCRIPTION OF THE DRAWINGS

FIG. 1(*a*) schematically shows the respective regions of the HTLV-I genome. FIG. 1(*b*) shows a plasmid constructed by incorporating the respective regions of the HTLV-I genome between the region encoding the CAT gene and the bovine growth hormone poly A signal (BGH pA) in a pRC/CMV-CAT vector.

FIG. 11 shows a comparison of conserved sequences of the amino acid sequences of the zinc finger domains of the TRP-1 protein according to the present invention.

FIG. 12 shows a comparison of amino acid sequences in the KRAB-A and KRAB-B domains of the TRP-1 protein according to the present invention and Kid-1.

Figure 2:
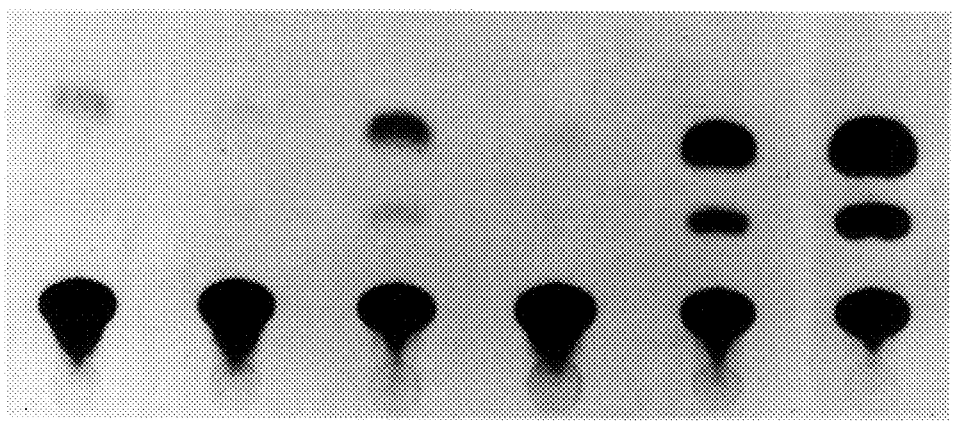
FIG. 2 is a thin layer chromatogram of a CAT activity assay for HeLa cells transfected with pRC/CMV-CAT plasmids into which the DNA sequences of the R1 to R5 regions of the HTLV-I genome are respectively incorporated.

BEST MODE FOR CARRYING OUT THE INVENTION (I) Definitions

Hereinafter, the terms that are employed for the description of the present invention will be explained.

"A Kruppel-type zinc finger domain" is a structural domain within a protein that is formed by a polypeptide chain being folded around a zinc atom. In general, the domain is found in a DNA binding protein, and is considered to be involved in the binding between the protein and DNA (Witzgall et al., Mol. Cell. Biol., 13(3): 1933–1942 (1993);

Constantinou-Deltas et al., Genomics, 12(3):581–9(1992); and Numoto et al., Nucl. Acids Res., 21(16): 3767–75 (1993)). For example, the protein (TRP-1) according to the present invention which binds to the transcriptional repressive region (U5RE; U5 Repressive Element) existing in the U5 region of human T-cell leukemia virus type I gene LTR includes five Kruppel-type zinc finger domains.

A "domain common to Kruppel-type transcriptional repressive factors" is a domain which is commonly found in Kruppel-type transcriptional repressive proteins and is considered to be involved in the repression of transcription of DNA (Witzgall et al., Proc. Natl. Acad. Sci. USA., 91(10): 4514–8 (1994); and Margolin et al., Proc. Natl. Acad. Sci. USA., 91(10): 4509–13 (1994)). In the present specification, such a domain will be referred to as a KRAB-A,B domain (Kruppel associated box-A,B domain).

A "sequence similar to" an amino acid sequence or a DNA sequence is not limited to any particular sequence, but is defined as such a sequence modified with substitutions, insertions, deletions, and the like known to those skilled in the art so that the function or activity of its encoded protein is substantially at the same level. Or, as long as the function or activity of the protein is substantially at the same level, it may contain chemical or biochemical modifications, or non-natural or derivatized amino acids or bases. For example, the above-mentioned TRP-1 protein preferably has similarity of about 50% or more, or homology of about 35% or more with the natural type. More preferably, the TRP-1 protein has similarity of about 70% or more, or homology of about 50% or more with the natural type. Still more preferably, the TRP-1 protein has similarity of about 80% or more, or homology of about 65% or more. Herein, "similarity" is defined as the rate (%) of identical amino acids within a similar sequence with respect to a reference sequence, where the amino acids are divided into the following five groups A to E and amino acids within each group are considered as identical; group A: Ala, Ser, Thr, Pro, and Gly; group B: Asn, Asp, Glu, and Gin; group C: His, Arg, and Lys; group D: Met, Leu, Ile, and Val; and group E: Phe, Tyr, and Trp. The "homology" of an amino acid sequence is defined as the rate (%) of identical amino acids within a similar sequence with respect to a reference sequence, where only completely identical amino acids are considered as identical. Furthermore, the "homology" of a DNA sequence is not limited to any particular sequence, but is defined as such a sequence modified with substitutions, insertions, deletions, and the like, known to those skilled in the art, especially so that the function of the DNA sequence, e.g., gene expression repressing function for HTLV-I, is substantially at the same level.

(II) Methods Which can be Used for the Present Invention

Methods known to those skilled in the art, e.g., those described in Molecular Cloning 2nd Edition (Maniatis et al., Cold Spring Harbor Laboratory, New York (1989)), can be adopted as general biochemical experimental procedures and molecular biological experimental procedures (electrophoresis of DNA, method for recovering DNA that has been electrophoretically separated from the gel, ligation, transformation of a host, culture of a recombinant host, preparation of plasmid DNA, cleavage of DNA by restriction enzyme, radiolabelling of DNA, and the like) to be used in the respective steps of the present invention.

A. Study of DNA molecules having a gene expression repressing function derived from HTLV-I (1) Construction of plasmids including various regions on the HTLV-I genome As HTLV-I-infected cell lines, MT-1, MT-2, MT-4, TL-Su, and H582 can be used, for example, as well as peripheral blood leukocytes from an ATL patient. The total RNA from these cells, cultured or uncultured, is extracted by an acid guanidium thiocyanate-phenolchloroform extraction method. After being annealed with random hexanucleotide primers, the extracted RNA is reacted with reverse transcriptase, whereby CDNA is prepared.

First, DNA sequences including various regions having appropriate lengths as indicated by R1 and the like in FIG. 1(a), for example, can be obtained by the known PCR method using an appropriate synthetic primer set corresponding to the desired regions, with the HTLV-I genomic DNA being used as a template. The primer may include a restriction site such as a Not I site, a Hind III site, an Apa I site, an Xba I site, or the like, at its 5' end so as to make it available for subsequent subcloning. The respective regions on the HTLV-I genome may be chemically or biochemically modified or contain non-natural or derivatized bases. Recombinant DNA sequences including sequences other than those DNA sequences which naturally occur are also provided by the present invention. Alternative forms of DNA sequences to natural DNA sequences are also provided; this includes but is not limited to those obtained through deletion, insertion, or substitution of one or more bases. Preferably, the DNA sequences have homology of 59% or more with the natural types.

The DNA sequences including the respective regions amplified by the PCR method, after recovery by gel-separation and cutting the desired sites by using restriction enzymes, can be incorporated into appropriate expression vectors in which a promoter, a gene sequence whose expression is to be adjusted, and the like, have been or can be incorporated. Preferably, the expression vector can be designed so as to contain a promoter, an expression repressive region of HTLV-I, RXE or RRE, and the like. More preferably, the expression vector can be designed so as to contain a promoter, a therapeutic gene sequence, an expression repressive region of HTLV-I, RXE or RRE, and the like. Depending on the purpose, the DNA sequences can be incorporated 5' upstream of a promoter, or at an appropriate position in the antisense orientation.

As expression vectors, eukaryotic expression vectors are used. Since mammalian cells (e.g., HeLa cells, Jurkat cells, COS cells, and CHO cells) are preferable as cells to be transfected with such expression vectors, vectors capable of being expressed in such selected cell lines are employed. Mammalian cell expression vectors, e.g., SV40-derived vector, bovine papilloma virus vector, herpes virus vector, adenovirus vector, pox virus vector, and retrovirus vector, can be used. Preferably, Jurkat cells are transfected by using a retrovirus vector.

As promoters, any known promoter can be used. Promoters which enhance the expression efficiency in virus-infected cells are preferable. Promoters which can be expressed in mammalian cells include, for example, cytomegalovirus immediate early promoter (CMV), viral LTR (long terminal repeat; e.g., HTLV-I, LTR, Rous sarcoma virus LTR, HIV-LTR), SV40 early promoter, and herpes simplex tyrosine kinase virus promoter. Preferable are viral LTR and CMV, the most preferable being viral LTR.

As a gene sequence whose expression is to be controlled, any one of various gene sequences can be used according to the specific purpose. For example, for the purpose of examining the expression repression activity of the respective regions of the HTLV-I genome, genes whose sequences encode proteins that can be expressed and easily detected are used. For example, a chloramphenicol acetyl transferase (CAT) gene, luciferase (Luc) gene, and the like can be used. For the purpose of attacking infected cells or preventing virus replication, gene sequences which can exhibit predetermined biological activities within infected cells (cells of an infected host) can be used. Gene sequences which can be toxic to infected cells or which can prevent virus replication are known as therapeutic genes in the field. Gene sequences which can be toxic to infected cells include toxic genes, e.g., diphtheria toxin A fragment (DT-A) gene and herpes simplex thymidine kinase (HSTK) gene. Gene sequences which can prevent virus replication include, for example, antisense nucleic acids, ribozymes, decoys, and trans dominant mutants.

As described later, RXE and RRE are regions which cancel the function of the gene expression repressive region in HTLV-I according to the present invention. In HTLV-I or HIV-I infected cell in which Rex or Rev protein acting on such regions is expressed, a cancellation mechanism works for the gene expression repression mechanism so as to enable the above-mentioned therapeutic gene to be expressed. Furthermore, RXE and RRE do not need to be regions derived from HTLV-I and HIV-I, respectively, but may alternatively be RXE, RRE, etc. from HTLV-II, HIV-II, etc.

Furthermore, poly A signal for adding poly A at the 3' end of mRNA can be introduced. For example, poly A signal of bovine growth hormone (BGHpA) or poly A signal of SV40 (SV40pA) can be used.

An expression vector having the above-mentioned sequences such as promoters can also be selected from among commercially available vectors, depending on the purpose, e.g., searching for repressive regions within the HTLV-I genome. In order to search for repressive regions within the HTLV-I genome, for example, pRC/CMV-CAT vector (manufactured by Invitrogen Inc.) can be used.

Plasmids can be constructed by incorporating respective regions of the HTLV-I genome into such an expression vector, e.g., at the Not I site shown in FIG. 1(b), by using a DNA Ligation Kit (Takara Shuzo Co., Ltd.). Each resultant plasmid can be confirmed to be a predetermined one by examining its base sequence using a T7 Sequencing Kit (manufactured by Pharmacia Biotech. These plasmids can be purified by transforming and culturing E. coli JM109 strain and subjecting it to cesium chloride density gradient centrifugation, for example.

(2) DNA Transfection

Appropriate cells can be transfected by using the respective plasmids obtain ed in (1) above as follows. For example, HeLa cells or Jurkat cells can be transfected with a mixture containing the above-mentioned plasmid and a pRC/CMV-Luc vector (CMV-Luc) containing the luciferase (Luc) gene following a known method (e.g., the lipofectin (GIBCO BRL) method). After the transfected cells a re cultured, a lysate is prepared and centrifuged to give supernatant. The luciferase activity of the supernatant due to CMV-Luc is measured by a known method (e.g., a method using a Lumat model LB9501 (manufactured by Berthold) which uses a PicaGene Kit (manufactured by Toyo Ink Co., Ltd.). The result can be used for the normalization of transfection efficiency.

(3) CAT Assay

The CAT activity in the supernatant obtained in (2) above, when transfected with a plasmid containing the chloramphenicol acetyl transferase gene, for example, can be measured by a known method in the art (Fordis et al., Methods in Enzymology, 151, 382–397(1987)). For example, chloramphenicol labeled with $^{14}C$ and acetyl CoA is added to the supernatant and incubated. Next, after extraction using ethyl acetate, the supernatant is concentrated and spotted on a thin layer chromatography (TLC) plate. This is developed in a development vessel saturated with a eveloping solution containing chloroform: methanol=95:5, and printed on an X-ray film by, for example, lacing it in contact with an imaging plate which is attached to a BioImage analyzer (manufactured by Fujix Co., Ltd.) for 1 hour. Thus, the rate of chloramphenicol that has been acetylated by the expressed CAT can be determined. Since acetylated chloramphenicol is more fat-soluble than chloramphenicol, it has a large Rf value on the normal-phase TLC plate. A higher CAT activity shown by this assay indicates a lower expression repression activity of the incorporated region. A lower CAT activity indicates a higher expression repression activity.

(4) Confirmation of the RNA amount transcribed from HTLV-I genome

The amounts of RNA transcribed from the plasmids containing the respective regions of the HTLV-I genome can be analyzed by Northern blotting as follows. Appropriate cells are transfected with the respective plasmids, and the total RNA is extracted. Next, RNA is subjected to electrophoresis using agarose-formaldehyde gel, and blotted onto a membrane (e.g., a nylon membrane or nitrocellulose membrane). For example, a plasmid containing the CAT gene can be hybridized with a probe labelled with $^{32}p$ or the like, using the CAT gene as a template, so that the CAT RNA amount can be detected with the use of an X-ray film. If the CAT RNA amount is large, then it is known that no repression is occurring on the transcription level.

(5) Construction of plasmids including regions of deletion mutagenesis

In order to investigate the central portion of the repression activity for the region exhibiting a high repression activity, plasmids can be constructed by deleting the region bidirectionally from both the 5' end and the 3' end, the resultant plasmid having such a subregion. First, in order to delete the region from the 5' end, a cleavage can be made at e.g., Not I, followed by blunting the end, and a further cleavage at the Eco NI site within the region, and then deletion using a deletion kit (manufactured by Takara Shuzo Co., Ltd.). On the other hand, the deletion from the 3' end can be made by cleavage with Apa I and Xba I followed by using the deletion kit. The thus-obtained regions of deletion mutagenesis are each incorporated into a vector. The CAT activity of the resultant plasmid can be measured for screening the minimum region required for the repression of the CAT activity. The central portion of the region responsible for the repression activity can be known because a deletion of a portion thereof would result in non-repression of the CAT activity.

(6) Clarification of the gene expression repression mechanism

As will become apparent from the following examples, a DNA sequence having a gene expression repressing function derived from HTLV-I exists in a region which is missing in a mutant provirus that is expressing p21X mRNA but exists in the genome of a complete provirus. The HTLV-I-derived gene expression repressive region is capable of allowing virus-infected cells to void elimination by the immune system by repressing the expression of the viral genes within an organism, thereby laying an important role in the latent infection mechanism of HTLV-I. Furthermore, the gene expression repressing function is also considered to play an important role in the mechanism of efficient replication of the virus because the gene expression repressing function can be cancelled by the expression of a sufficient amount of Rex protein.

B. Study of proteins which bind to the transcriptional repressive regions of HTLV-I gene (1) Cloning of cDNA for TRP-1

Hereinafter, the cloning of DNA fragments including DNA encoding TRP-1, which is the protein provided by the present invention, as well as the sequencing method will be exemplified. The sequence of such a DNA fragment can be determined by, for example, screening a CDNA library of Molt-4 cells, Jurkat cells, CEM cells, etc.—which are cell lines from the peripheral blood of patients with acute lymphocytic leukemia—by using a DNA having several U5REs linked together as a probe, and analyzing the DNA resulting from the screening by DNA sequencing.

(1.1) Preparation of a DNA probe

The protein provided by the present invention, namely TRP-1, binds to U5RE. Therefore, a probe having a DNA sequence corresponding to U5RE can be used as a probe for screening TRP-1 by the South Western method. The probe can be prepared as follows, for example: First, DNA fragments synthesized so as to include U5RE is purified, heat-denatured, and thereafter made into a double-stranded DNA. Next, the resultant double-stranded DNA is ligated so as to give a double-stranded DNA including a sequence having several U5REs linked together. After incorporating this into an appropriate plasmid (e.g., pSL1180, pUC118, or pU19), it is used as a template for PCR amplification. By conducting PCR in the presence of $^{32}$P-dCTP for radiolabelling, a probe for use in the South-Western method can be obtained.

(1.2) Screening of a library

As a library to be screened for DNA encoding TRP-1, various libraries of cells can be used such as Molt-4 cells, Jurkat cells, CEM cells, etc., which are cell lines from the peripheral blood of patients with acute lymphocytic leukemia. For example, a cDNA library of pSport 1 of the human acute lymphocytic leukemia cell line Molt-4 can be made as follows: First, RNA can be extracted from Molt-4 cells by a guanidine thiocyanate method (Chomczynski et al., Anal. Biochem. 162, 156–159 (1987)). From the RNA, mRNA can be obtained by using e.g., oligotex (manufactured by Takara Shuzo Co., Ltd.) or an Oligo dT Agarose column. From the mRNA, cDNA can be made by using e.g., Superscript cDNA Synthesis System (BRL), and a cDNA library in which the cDNA is incorporated in an appropriate expression vector can be created.

Next, the resultant cDNA library is introduced into an appropriate host, e.g., E. coli, plated on petri dishes and in con tact with an appropriate membrane such as to allow protein s to be expressed. Screening can be performed by utilizing as an indicator the DNA binding activity of the above-mentioned probe to the proteins produced from the thus-prepared cDNAs fixed on a nitroceullose membrane.

Furthermore, the cDNA library can be subjected to screening by colony hybridization, plaque hybridization or the like using a cDNA fragment prepared from a cDNA clone obtained through the above-mentioned screening as a probe.

(1.3) Determination of base sequences of the clones

The determination of base sequences of the insert of the clone obtained by screening a library can be conducted by a dideoxy method (Sanger, Science, 214, 1205–1210(1981)), for example. The DNA sequence and amino acid sequence of TRP-1, as obtained by analyzing such clones, is shown as SEQ ID NO:15 in the Sequence Listing.

(2) Expression of recombinant TRP-1 and analysis of binding with U5RE

The gene encoding TRP-1 according to the present invention is incorporated into an appropriate vector, e.g., pRSET, pAM82, or pCDM8 to give an expression vector for expressing TRP-1.

The expression vector is introduced into, for example, a bacterium, yeast, insect cell, or animal cell, whereby a transformant is created. By culturing the transformant, TRP-1 according to the present invention can be produced.

For example, an expression vector including the TRP-1 gene according to the present invention is created by incorporating the gene into the KpnI-NotI site of pRSET. A transformant can be created by introducing this into E. coli BL12 strain. A fusion protein having oligohistidine at its amino end can be expressed by the transformant. The culture product of TRP-1 thus obtained can be purified by the affinity column method or the like.

The binding analysis between TRP-1 and U5RE can be made as follows, for example: U5RE DNA labelled with $^{32}$P and the purified above-mentioned recombinant TRP-1 are reacted in a binding reaction buffer in the presence of poly d(I-C); the reaction solution is subjected to electrophoresis on polyacrylamide gel; the gel is dried on a paper filter, and thereafter the binding can be analyzed by autoradiography.

(3) Confirmation of the tissue distribution of TRP-1

The tissue distribution of TRP-1 can be confirmed by, for example, analyzing the expression of mRNA or the expression of TRP-l. The expression of mRNA can be confirmed by a Northern blot analysis using CDNA. The expression of TRP-1 can be confirmed by Western blot analysis after creating antibodies against TRP-1.

(4) Functional analysis of TRP-1

Since TRP-1 is considered to be involved in transcription repression by binding to U5RE, the functional analysis thereof can be made as follows: For example, an expression vector which is capable of expressing TRP-1 and an expression vector in which the U5RE gene and a gene to serve as an indicator of expression are incorporated, are simultaneously introduced into an appropriate cell. By culturing this and measuring the expression of the indicator gene, it can be confirmed whether or not TRP-1 represses expression via U5RE.

As the gene to serve as an indicator, a gene such that the expression of a protein encoded by the gene sequence can be easily detected is employed. For example, chloramphenicol acetyl transferase (CAT) gene, luciferase (Luc) gene, or the like can be employed.

EXAMPLES

Example 1

(1) Construction of plasmid for analyzing the presence/absence of a gene expression repression action in each region on the HTLV-I genome.

As shown in FIG. 1, the regions on the HTLV-I genome for which the presence/absence of a gene expression repression action were analyzed are: R1 (positions 1351–3182 in SEQ ID NO:1 in the Sequence Listing), R2 (positions 3165–4984 in SEQ ID NO:1 in the Sequence Listing), R3 (positions 4951–6635 in SEQ ID NO:1 in the Sequence Listing), R4 (positions 2268–4078 in SEQ ID NO:1 in the Sequence Listing), R5 (positions 4061–5782 in SEQ ID NO:1 in the Sequence Listing), R6 (positions 1351–2268 in SEQ ID NO:1 in the Sequence Listing), R7 (positions 2268–3182 in SEQ ID NO:1 in the Sequence Listing), R8 (positions 3165–4080 in SEQ ID NO:1 in the Sequence Listing), and R9 (positions 4061–4984 in SEQ ID NO:1 in the Sequence Listing). Region R21 (positions 7302–8201 in SEQ ID NO:1 in the Sequence Listing), which is not considered to have any repression action because it is not missing from the mutant provirus, was used as a negative control for comparison. As for the base numbers and compositions of the nucleotides, those of a published HTLV-I ATK clone were used (Seiki et al., Proc. Natl. Acad. Sci. USA., 80, 3618–3622(1983)). FIG. 1(a) schematically shows the respective regions of the HTLV-I genome. Portions shown as rectangles represent LTRs and respective structural genes of HTLV-I. ▼ represents a splice donor signal. ▼ represents a splice acceptor signal. FIG. 1(b) is a schematic diagram showing a plasmid pRC/CMV-CAT for examining gene expression repression action. $P_{CMV}$ represents a CMV promoter. $BGH_pA$ represents a bovine growth hormone poly A signal. The broken line in FIG. 1(b) indicates that gene sequences on the HTLV-I genome can be incorporated at the position.

The respective regions of the HTLV-I genome were obtained by synthesizing the primers shown in Table 1 below, and using them in combination with genomic DNA of an HTLV-I-infected cell line TL-Su as a template in a PCR method. A Not I site was provided at the 5' end of each primer so as to be available for later subcloning.

TABLE 1

| Amplified region | Primers used | |
| --- | --- | --- |
| R 1 region | 1 3 5 1 F N (SEQ ID No:2) | 3 1 8 2 R N (SEQ ID No:8) |
| R 2 region | 3 1 6 5 F N (SEQ ID No:4) | 4 9 8 4 R N (SEQ ID No:10) |
| R 3 region | 4 9 5 1 F N (SEQ ID No:6) | 6 6 3 5 R N (SEQ ID No:12) |
| R 4 region | 2 2 6 8 F N (SEQ ID No:3) | 4 0 7 8 R N (SEQ ID No:9) |
| R 5 region | 4 0 6 1 F N (SEQ ID No:5) | 5 7 8 2 R N (SEQ ID No:11) |
| R 6 region | 1 3 5 1 F N (SEQ ID No:2) | 2 2 6 8 R N (SEQ ID No:7) |
| R 7 region | 2 2 6 8 F N (SEQ ID No:3) | 3 1 8 2 R N (SEQ ID No:8) |
| R 9 region | 4 0 6 1 F N (SEQ ID No:5) | 4 9 8 4 R N (SEQ ID No:10) |
| R 2 1 region | 7 3 0 2 F N (SEQ ID No:13) | 8 2 0 1 R N (SEQ ID No:14) |

In order to amplify each region of the HTLV-I genome, a PCR reaction was performed as follows: First, 0.5 μg of genomic DNA of HTLV-I-infected T cell line TLSu, 100 pmol/tube of each primer, 10 μl of 10×PCR reaction buffer, 5 units of AmpliTaq DNA polymerase, and dNTPs having final concentrations of 200 μM were added in a tube, and finally sterilized distilled water was added to 100 μl. After the reaction was performed for 5 minutes at 94° C., a reaction cycle of 1 minute at 94° C., 1 minute at 50° C., and 2 minutes at 72° C. was repeated 30 times, followed by 7 minutes at 72° C. After being separated on agarose gel, a piece of gel containing each amplified region was cut and recovered by using SUPREC-01 manufactured by Takara Shuzo Co., Ltd. The purified DNA fragments from the respective regions were, after being processed with Not I restriction enzyme (manufactured by Takara Shuzo Co., Ltd.), incorporated at the Not I site of a pRC/CMV-CAT vector (manufactured by Invitrogen Inc.; hereinafter CMV-CAT) by using a DNA Ligation Kit (manufactured by Takara Shuzo Co., Ltd.) to give the plasmids including the DNA sequences of the respective regions shown in Table 1 above (respectively referred to as, CMV-CAT-R1, CMV-CAT-R2, CMV-CAT-R3, CMV-CAT-R4, CMV-CAT-R5, CMV-CAT-R6, CMV-CAT-R7, CMV-CAT-R9, and CMV-CAT-R21). CMV-CAT-R8, which is a plasmid including the DNA sequence of the R8 region, was obtained by cleaving the Xba I site (base number 4080 in SEQ ID NO:1 in the Sequence Listing) located approximately in the center of R2 and the Xba I site immediately 3' to the Not I site of CMV-CAT by using Xba I (manufactured by Takara Shuzo Co., Ltd.) and removing about ½ of the 3' side of R2, followed by self-ligation.

The plasmids (CMV-CAT-R7-RXE, CMV-CAT-R8-RXE, and CMV-CAT-R21-RXE) into which RXEs (Rex responsible element) are incorporated immediately 3' downstream of R7, R8, and R21 were obtained by incorporating RXE (base numbers 319–620 in SEQ ID NO:1 in the Sequence Listing) (Toyoshima et al., J. Virol., 64, 2825–2832 (1990)), which was obtained by a PCR method using the TL-Su cell genomic DNA as a template, at the Apa I site or the Xba I site of CMV-CAT-R7, CMV-CAT-R8, and CMV-CAT-R21. To obtain pRC/CMV-luciferase (hereinafter referred to as CMV-Luc), a luciferase gene, which was obtained by a PCR method using PGV-C vector plasmid (manufactured by Toyo Ink Mfg. Co., Ltd.) as a template, was incorporated at the Hind III site of pRC/CMV vector. Furthermore, SRα-rex plasmid was obtained by incorporating rex CDNA into pCD-SRα vector (Orita et al., J. Gen. Virol., 73, 2283–2289 (1992)).

The base sequence of each plasmid was examined by using a T7 Sequencing Kit (manufactured by Pharmacia Biotech), thereby confirming each to be the desired plasmid. Each of the transformants of E. coli JM109 with the respective plasmids was cultured for 16 hours at 37° C. in 200 ml of 2YT medium, and purified by performing cesium chloride density gradient centrifugation twice, following a conventional method.

(2) CAT assay study as to the presence/absence of gene expression repression activity in each region on the genome Two μg of CMV-CAT as a parent vector and an equivalent molar amount of each plasmid obtained in (1) above were placed in a tube. One μg of CMV-Luc and pBluescript vector were added to each tube so that the amounts of plasmid in the respective tubes became equal. Furthermore, an Opti-MEM medium (manufactured by GIBCO BRL, Inc.) was added to a final volume of 100 μl. A mixture of 15 μl of Lipofectin (manufactured by GIBCO BRL, Inc.) and 85 μl of the Opti-MEM medium was added to the tubes and left at room temperature for 15 minutes. The mixed solution was added to HeLa cells ($3 \times 10^5$/well) or Jurkat cells ($3 \times 10^5$/well) in a 6-well dish (both in 3 ml of the Opti-MEM medium) for transfection. After 6 hours for the HeLa cells and 16 hours for the Jurkat cells, the media were replaced with normal serum-containing media (i.e., E-MEM+10% heat-inactivated fetal bovine serum for HeLa cells, and RPMI+10% heat-inactivated fetal bovine serum for Jurkat cells) followed by incubation for 48 hours. Thereafter, each kind of cells were collected and a lysate was prepared with 300 μl of Reporter lysis buffer (manufactured by Stratagene, Inc.). These lysates were centrifuged at 12000 rpm for 5 minutes to obtain supernatant, certain amounts of which were subjected to measurement of luciferase activity derived from CMV-Luc, by means of a Lumat model (manufactured by Berthold) using a PicaGene Kit (manufactured by Toyo Ink Co., Ltd.).

Based on the results obtained, the transfection efficiency was corrected, and the supernatant amount to be used for CAT activity measurement was determined. Next, the determined amount of supernatant was placed in a tube, to which a ×1 Reporter lysis buffer was added to a final volume of 122 µl. $^{14}$C-chloramphenicol (manufactured by New England Nuclear Inc.) and 20 µl of acetyl CoA (4 mM) were added to the above, which was left for 1 hour at 37° C. after mixing. Next, after extraction with 500 µl of ethyl acetate, it was concentrated with a centrifugation evaporator, and spotted on a TLC plate (DC-Alufolien Keiselgel 60 F254, manufactured by MERCK & Co., Inc.). This was developed in a developing vessel saturated with a developing solvent of chloroform: methanol=95:5. Then, it was placed in contact with an imaging plate attached to a BioImage analyzer (manufactured by Fujix Co., Ltd.) for 1 hour, and printed on an X-ray film (XAR5, manufactured by Eastman Kodak Co.). Thus, the rate of acetylation was determined based on the Rf values of radioactivity corresponding to chloramphenicol and acetylated chloramphenicol.

First, the presence/absence of gene expression repression activity was studied for the five regions R1 to R5, which are substantially equivalent to the regions missing in a deletion-type virus in the HTLV-I-infected cell line capable of expressing p21X mRNA, with an assay system utilizing the expression of the CAT gene as an indicator using HeLa cells. The results are shown in FIG. 2. The respective lanes represent the CAT activity of HeLa cells transfected with CMV-CAT-R1 (lane 1), CMV-CAT-R2 (lane 2), CMV-CAT-R3 (lane 3), CMV-CAT-R4 (lane 4), CMV-CAT-R5 (lane 5), and CMV-CAT (lane C) in an amount in moles equivalent to 2 µg of CMV-CAT. The numerals below indicate the rate (percent) of acetylated chloramphenicol. Since HeLa cells which were transfected with CMV-CAT-R1, CMV-CAT-R2, and CMV-CAT-R4 exhibited remarkably low CAT activity, it was found that the R1, R2, and R4 regions exhibit strong repression activity. The R3 region exhibited intermediate repression activity.

Figure 3:
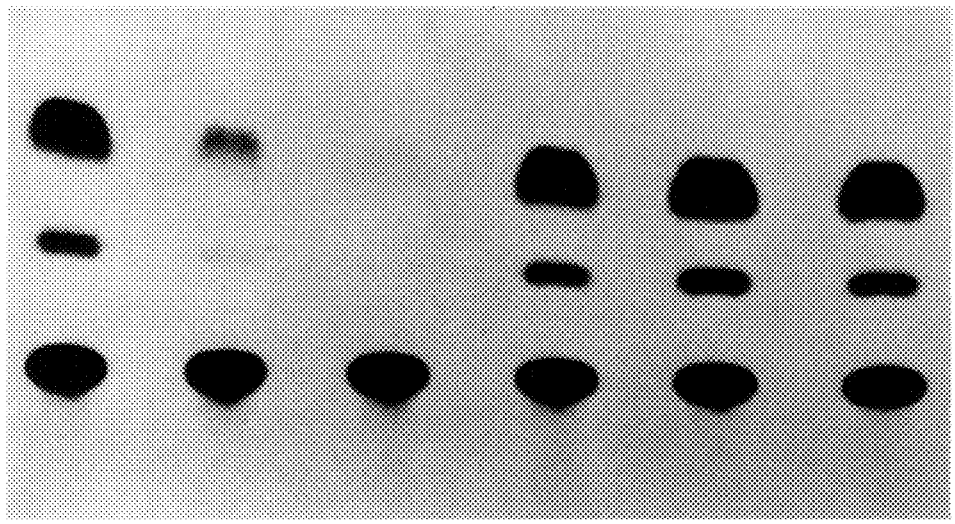
FIG. 3 is a thin layer chromatogram of a CAT activity assay for HeLa cells transfected with pRC/CMV-CAT plasmids into which the DNA sequences of the R6 to R9 and the R21 regions of the HTLV-I genome are respectively incorporated.

Therefore, the repression activity in the four regions R6 to R9, into which the region encompassing R1, R2, and R4 is further divided (see FIG. 1(a)), was studied. The results are shown in FIG. 3. The respective lanes represent the CAT activity of HeLa cells transfected with CMV-CAT-R6 (lane 1), CMV-CAT-R7 (lane 2), CMV-CAT-R8 (lane 3), CMV-CAT-R9 (lane 4), CMV-CAT-R21 (lane 5), and CMV-CAT (lane C) in an amount in moles equivalent to 2 pg of CMV-CAT. The numerals below indicate the rate (percent) of acetylation. It was found that since HeLa cells transfected with CMV-CAT-R7 and CMV-CAT-R8 exhibit low CAT activity, the R7 and R8 regions exhibit strong repression activity. However, the R21 region transcribed to the p21X mRNA used as a negative control and the R6 and R9 regions showed no or very weak repression activity.

Accordingly, it was proven that the repression activity of the R1 region derives from the R7 region, the repression activity of the R2 region from the R8 region, and the repression activity of the R4 region from R7 and R8. A similar experiment using Jurkat cells derived from T cells, which define a host for HTLV-I, showed similar results, whereby it was confirmed that the R1, R2, R4, R7, and R8 regions exhibit repression action. Thus, two viral gene expression regions (R7 and R8) were found in the pol region.

Example 2

Study of the Mechanism of Gene Expression Repression Activity in the R7 and R8 Regions (1) Study of post-translational influence The mechanism of gene expression repression activity in the R7 and R8 regions was studied as follows by Northern blotting for the amount of CAT RNA transcribed from CMV-CAT-R7 and CMV-CAT-RB:

HeLa cells (1.5×10⁶/dish) in a petri dish (φ: 10 cm) were transfected with plasmids, namely, 18.30 µg of CMV-CAT-R7, 18.24 µg of CMV-CAT-R8, 18.34 µg of CMV-CAT-R9, and 16 µg of CMV-CAT, and the total RNA was extracted 40 hours later by using an ISOGEN reagent (manufactured by Nippon Gene Co., Ltd.). Next, 15 µg of each was subjected to electrophoresis on 1% or 1.5% agarose in a MOPS buffer solution (20 mM MOPS[3-(N-morpholino)-propanesulphonic acid] pH 7.0, 5 mM sodium acetate, and 0.5 mM EDTA) gel in the presence of 0.66 M formaldehyde, and blotted onto a nylon membrane (Hybond-N+, manufactured by Amersham, Inc.) by capillary transfer using 20×SSC. Alkaline fixation was performed following a conventional method. Hybridization with a $^{32}$P-labelled probe prepared with a Multiprime Labelling Kit (manufactured by Amersham, Inc.) by using the CAT gene as a template was performed at 68° C. for 2 hours. Quick Hyb. reagent (manufactured by Stratagene, Inc.) was used as a hybridization solution. The washing of the membrane was performed by two 15-minute washes with 2×SSC, 0.1% SDS solution at room temperature, and subsequently one 30-minute wash with 0.1×SSC, 0.1% SDS solution at 60° C. The detection of the signal was performed at −80° C. for 40 hours, using an X-ray film XAR5 manufactured by Eastman Kodak Co. with an intensifying screen.

Figure 4:
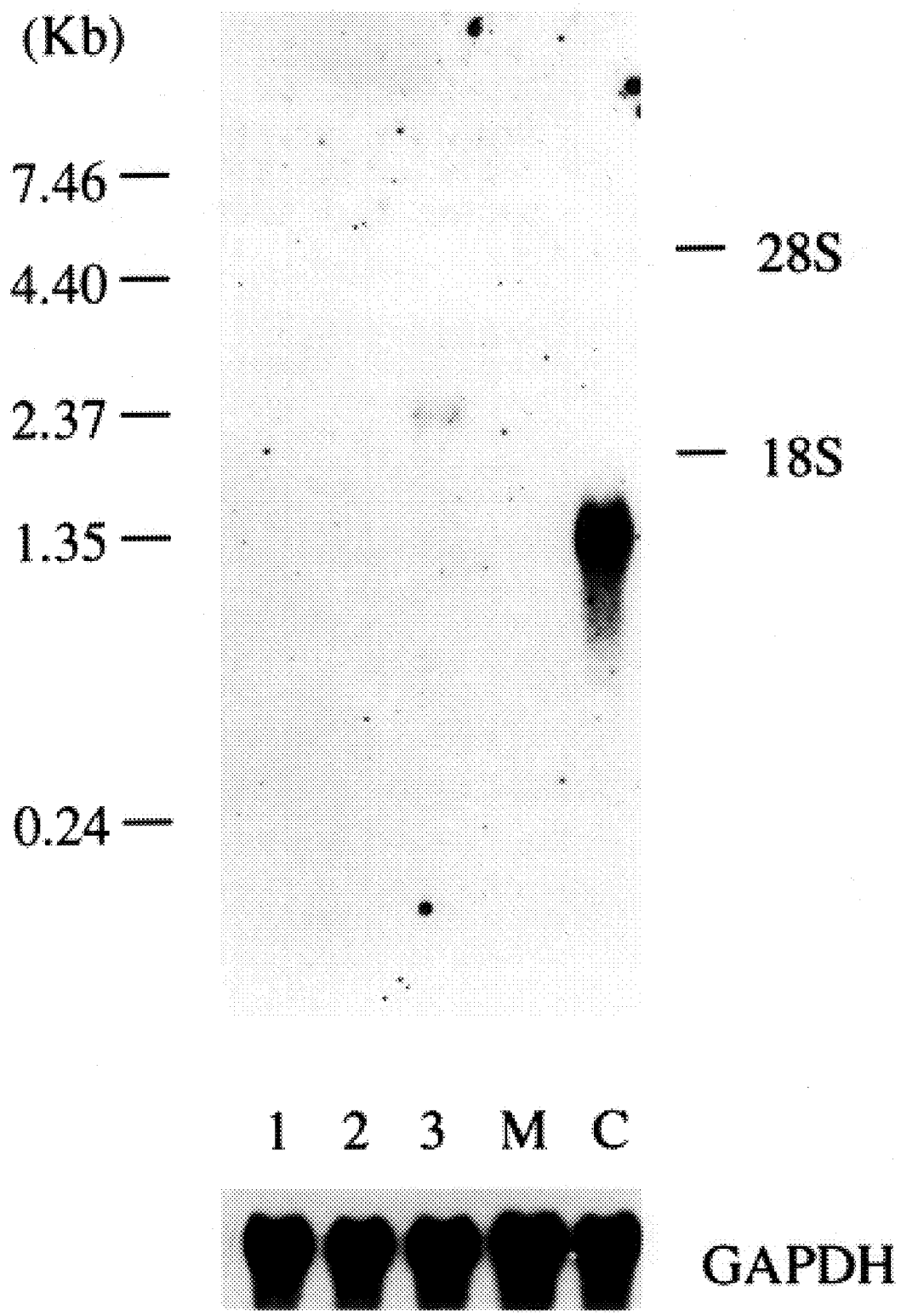
FIG. 4 shows results of a Northern blotting analysis of HeLa cells transfected with pRC/CMV-CAT plasmids into which the DNA sequences of the R7 to R9 of the HTLV-I genome are respectively incorporated, the analysis using the CAT gene as a template for a probe.

The results are shown in FIG. 4. The respective lanes represent the results of Northern blotting for HeLa cells transfected with CMV-CAT-R7 (lane 1), CMV-CAT-R8 (lane 2), CMV-CAT-R9 (lane 3), and CMV-CAT (lane C) obtained by hybridization of the membranes with a probe prepared by using the CAT gene as a template. The band shown at GAPDH indicates a result of hybridization with a probe prepared by using the GAPDH (glyceraldehyde 3-phosphate dehydrogenase) gene as a template. Based on this, the equivalence of the amount of RNA on the membrane was verified. The RNA of untransfected HeLa cells was used for lane M. In HeLa cells transfected with substantially the same molar amount of plasmids, no CAT RNA from CMA-CAT-R7 and CMA-CAT-R8 (predicted size: about 2.3 kb) was detected, indicative of a remarkably small amount. However, it was possible to detect the CAT RNA from CMA-CAT-R9 including the R9 region (predicted size: about 2.3 kb), which showed little repression action in Example 1 and the CAT RNA from the control CMV-CAT (predicted size: about 1.3 kb). Therefore, it was revealed that the repression by the R7 and R8 regions occurs before or at the RNA level, and not post-translationally.

(2) Study at the transcriptional level

The two presumable mechanisms for causing a decrease in the expressed RNA amount are as follows: One is a mechanism by which the R7 and R8 regions function in cis as transcription repressors to repress the transcription level from the CMV promoter. The other is a mechanism where the decrease is due to poor stability in RNA including the R7 and R8 regions while the transcription level from the CMV promoter remains unchanged. In general, a transcription repressor is indifferent to the distance to a promoter, position, or the directionality of sense or antisense. Therefore, plasmids were constructed for examination which incorporated the R1, R2, and R4 regions in the sense or antisense orientation immediately 5' upstream of the CMV promoter. As a result, no repression activity was observed in these cases. Therefore, the decrease is not considered to be occurring at the transcriptional level.

(3) Study of post-transcriptional influence

It is known that HTLV-I Rex binds to RXE on the viral mRNA and functions after transcription to repress splicing of the viral mRNA and enhances the transport from the nucleus to the cytoplasm. Accordingly, the influence of the post-transcriptional action of Rex on the repression action of the regions R7 and R8 was studied. For this purpose, plasmids (CMV-CAT-R7-RXE (+ or −), CMV-CAT-R8-RXE (+ or −), and CMV-CAT-R21-RXE (+ or −)) were constructed by incorporating RXE in the sense (+) or antisense (−) orientation immediately 3' down-stream of the genomic regions in CMV-CAT-R7, CMV-CAT-R8, and CMV-CAT-R21 so as to be transcribed to RNA.

Figure 5:
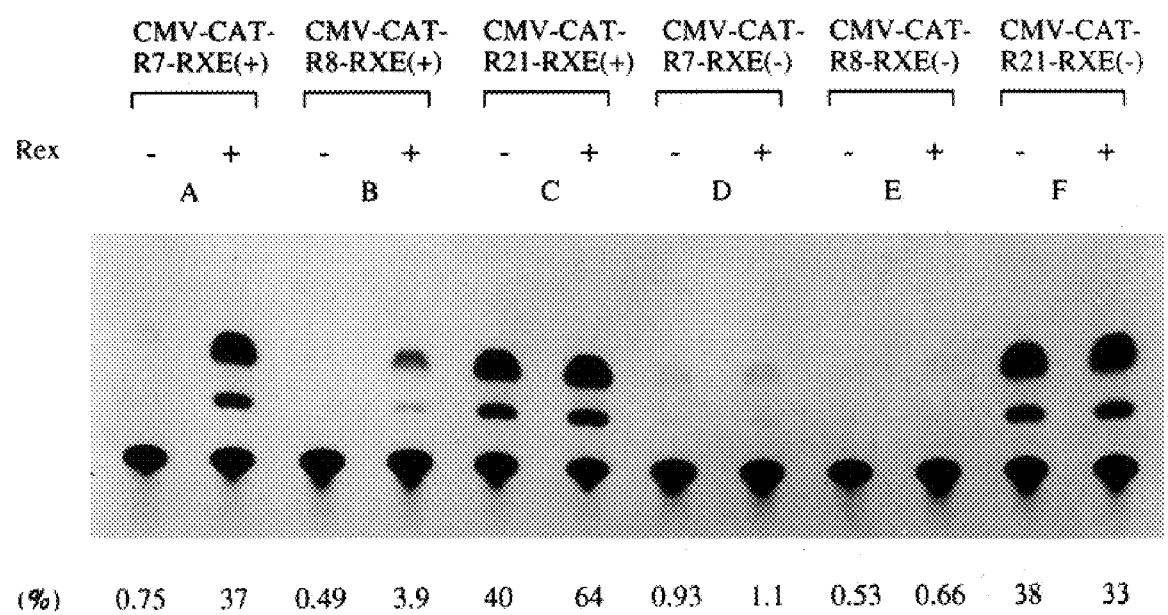
FIG. 5 is a thin layer chromatogram of a CAT activity assay for HeLa cells transfected with plasmids obtained by incorporating RXEs in the sense (+) or antisense (−) orientation 3' downstream of the DNA sequences of the R7, R8 and R21 regions of the HTLV-I genome in pRC/CMV-CAT plasmids into which the sequences have been respectively incorporated.

HeLa cells were co-transfected with these plasmids and SRα-rex plasmid expressing Rex, and the CAT activity thereof was measured. The results are shown in FIG. 5. The blocks (each consisting of two lanes) denoted by brackets in the figure indicate the CAT activity of HeLa cells which were co-transfected with 2 μg each of: CMV-CAT-R7-RXE (+) (block A), CMV-CAT-R8-RXE(+) (block B), CMV-CAT-R21-RXE(+) (block C), CMV-CAT-R7-RXE(−) (block D), CMV-CAT-R8-RXE(−) (block E), or CMV-CAT-R21-RXE(−) (block F) and 1.5 μg of pCD-SRα-rex(Rex+) or 1.5 μg of pCD-SRα(Rex−). The numerals below indicate the rate (percent) of acetylation of chloramphenicol. As shown in FIG. 5, the repression action of the R7 and R8 regions is remarkably inhibited only in the case where the RXE is in the sense orientation in the presence of rex (Rex+), indicative of recovery of the CAT activity, as seen from the results of blocks A and B. Thus, it was revealed that the repression action of the R7 and R8 regions is effectively cancelled by a post-transcriptional action by Rex via binding to RXE.

Figure 6:
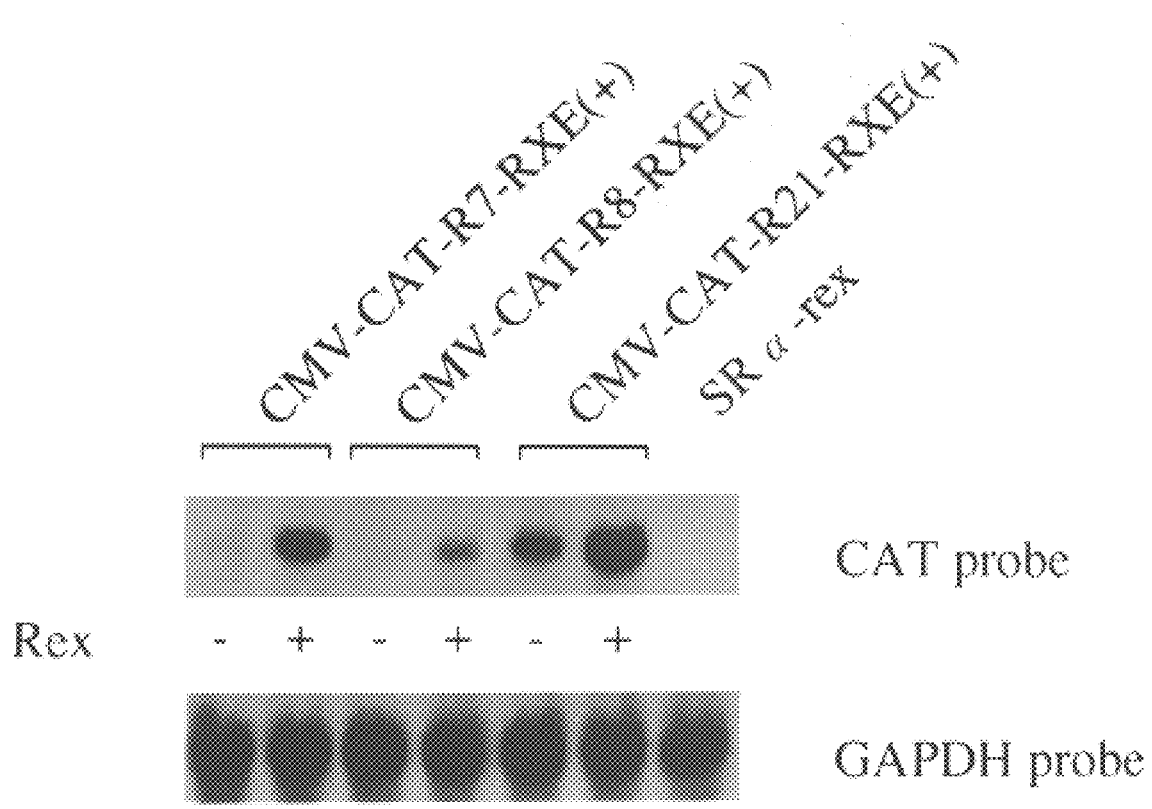
FIG. 6 shows results of a Northern blotting analysis of HeLa cells transfected with plasmids obtained by incorporating RXEs in the sense (+) or antisense (−) orientation 3' downstream of the DNA sequences of the R7, R8 and R21 regions of the HTLV-I genome in pRC/CMV-CAT plasmids into which the sequences have been respectively incorporated, the analysis using the CAT gene as a template for a probe.

Next, HeLa cells were co-transfected with 6 μg of CMV-CAT-R7-RXE(+), 6 μg of CMV-CAT-R8-RXE(+), or 6 μg of CMV-CAT-R21-RXE(+) and 9 μg of pCD-SRα-rex(Rex+) or 9 μg of pCD-SRα(Rex−), so that the total RNA was obtained 40 hours later. These were subjected to electrophoresis in 1.5% denaturing aldehyde gel. A Northern blotting was conducted. Membranes were hybridized with a probe prepared by using the CAT gene as a template (FIG. 6). Next, hybridization was performed with a probe prepared by using the GAPDH gene as a template. Based on this, the equivalence of the amount of RNA on the membrane was verified (the band shown at GAPDH). The lane indicated as SRα-rex in FIG. 6 represents those transfected only with 9 μg of SRα-rex. The results coincided with the aforementioned CAT activity results.

Furthermore, it was also confirmed that HTLV-I tax, which is known to activate the LTR of HTLV-I in trans to enhance transcription, has no influences on the repression action of the R7 and R8 regions. The above results were considered to indicate that the repression action of the R7 and RB regions is exercised primarily after transcription Example 3

Study of Gene Expression Repressive Activity Regions (1) Construction of plasmids including deletion mutagenized regions.

In order to investigate the central portion of the repression activity of the R8 region, which exhibited the stronger repression activity among both repression activity exhibiting regions R7 regions and RB, plasmids were constructed by deleting R8 in CMV-CAT-R8 bidirectionally from both the 5' end and the 3' end, the resultant plasmid having such a subregion. First, in order to delete R8 from the 5' end, CMV-CAT-R8 was cleaved with Not I (manufactured by Takara Shuzo Co., Ltd.), followed by blunting the end with a DNA Blunting Kit (manufactured by Takara Shuzo Co., Ltd.), and a further cleavage at the Eco NI site within the R8 region (base number 3362 in SEQ ID NO:1 in the Sequence Listing) was made for deletion with a Deletion Kit for Kilo-sequence (manufactured by Takara Shuzo Co., Ltd.). On the other hand, in order to delete R8 from the 3' end, CMV-CAT-R8 was cleaved with Apa I (manufactured by Takara Shuzo Co., Ltd.) and Xba I (manufactured by Takara Shuzo Co., Ltd.) for deletion with a Deletion Kit for Kilo-sequence. The degree of deletion was determined by using a T7 Sequencing Kit (manufactured by Pharmacia Biotech.).

Figure 7:
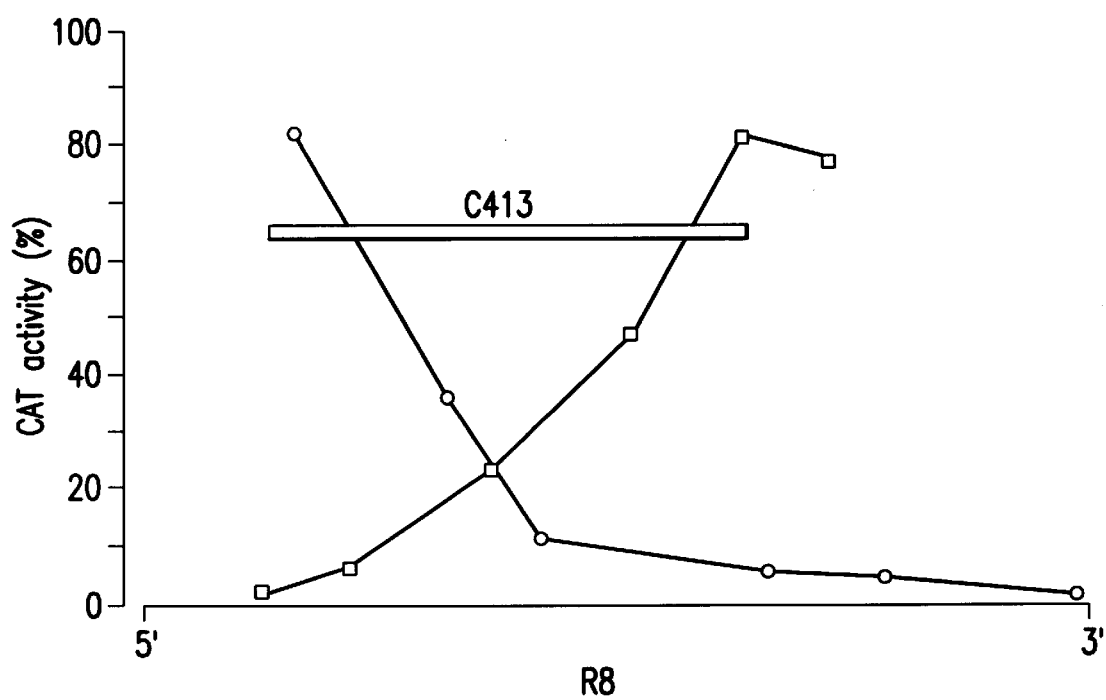
FIG. 7 is a graph showing the CAT activity of HeLa cells transfected with pRC/CMV-CAT plasmids into which the DNA sequences of deletion mutagenized regions obtained by deleting R8 of the HTLV-I genome from the 5' side or the 3' side are respectively incorporated.

(2) Measurement of the CAT activity of plasmids having deletion mutagenized regions The CAT activity of plasmids having deletion mutagenized regions obtained in (1) above was measured. The results are shown in FIG. 7. These plasmids are obtained by deleting the R8 region from the 5' end (□) or the 3' end (○). A region consisting of 413 bp (C413) which is considered as a central region of activity of R8 from these results is shown in FIG. 7. The vertical axis of FIG. 7 represents the CAT activity, whereas the horizontal axis represents the R8 region. It was found that, as the deletion progresses, the CAT activity is gradually recovered from a low activity state due to the R8 region. Therefore, it is considered that the full expression of the repression activity of the R8 region requires a large region or small centers of activity being dispersed over a large area.

Moreover, since strong repression activity is maintained after deleting the 5'-end region (a region on the 3'-end side of the R7 region that overlaps with the R8 region), it is apparent that the R7 and R8 regions are two independent gene expression repressive regions.

Figure 8:
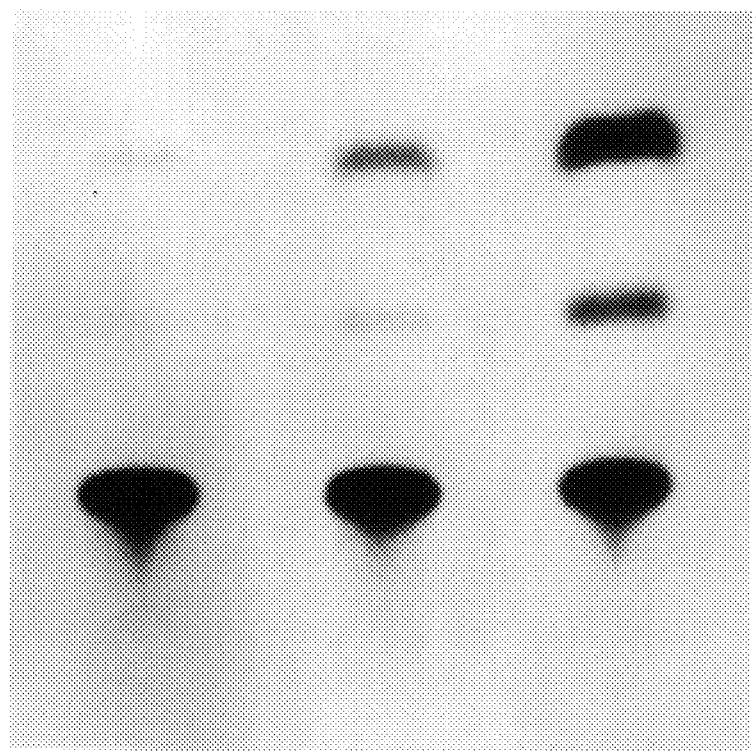
FIG. 8 is a thin layer chromatogram of the CAT activity of HeLa cells transfected with pRC/CMV-CAT plasmids into which C413 or N413 is incorporated in the sense or antisense orientation.

The repression activity of the 413 bp in the central portion (base numbers 3368–3780 in SEQ ID NO:1 in the Sequence Listing, hereinafter C413), whose deletion led to a remarkable recovery of the CAT activity, was examined. The results are shown in FIG. 8. They show comparison between the CAT activity of HeLa cells transfected with CMV-CAT-C413 sense (lane 1), CMV-CAT-C413 antisense (lane 2), CMV-CAT-N413 (lane 3) in an amount in moles equivalent to 2 μg of CMV-CAT. The numerals below indicate the rate (percent) of acetylation of chloramphenicol. CMV-CAT-C413 having C413 strongly repressed the CAT activity as compared with CMV-CAT-N413 having a region of 413 bp in the R21 region (base numbers 7302–7714 in SEQ ID NO:1 in the Sequence Listing, hereinafter N413) as a control. It was further found that C413 shows significantly stronger repression activity when incorporated in the sense orientation. Again, it was suggested that the repression action of the R8 region occurred after transcription. Thus, since a region with a stronger repression action requires a relatively long region for sufficient expression of the repression action, and the repression action is attenuated in the antisense orientation, it is considered that the repression action is a posttranscriptional regulatory mechanism which requires the region to be transcribed and take a certain higher-order structure.

(3) Study of homology in regions of gene expression repression activity

HTLV-I is an Oncovirus among retroviruses. Known closely-related viruses are simian T-cell leukemia virus type I (STLV-I), HTLV-II, and bovine leukemia virus (BLV)

(Weiss, et al. RNA TUMOR VIRUSES: Molecular Biology of Tumor Viruses, 2nd edition, 405–485, Cold Spring Harbor Laboratory (1985)). On the other hand, HIV is also a retrovirus but is a Lentivirus and therefore is taxonomically distant. It is know that STLV-I, HTLV-II and BLV, as in the case of HTLV-I, chronically infect a host throughout the host's life and that the expression of the viral genes are strongly repressed in organisms. The inventors have found mRNA having the same properties as those of p21X mRNA of HTLV-I in STLV-I, HTLV-II, or BLV-infected cells (Orita et al., VIRUS GENES, 7, 197–204 (1993)). Therefore, it is expected that STLV-I, HTLV-II, and BLV also include DNA sequences having gene expression repression activity. Therefore, the homology with the gene expression repressive sequence of HTLV-I (positions 2260–4080) was analyzed for viruses whose entire DNA sequence is known, namely, HTLV-II (Shimotohno et al., Proc. Natl. Acad. Sci. USA., 82, 3101–3105(1985)), BLV (Sagata et al., Proc. Natl. Acad. Sci. USA., 82, 677–681(1985)), and HIV as a negative control (Adachi et al., J. Virol., 59, 284–291 (1986)). The analysis was performed by using a DNA Maximum Homology analysis software of DNASIS (Hitachi Software Engineering Co., Ltd.) and GenBank as a database.

As a result of the homology analysis, HTLV-II and BLV exhibited homology of 65% and 59%, respectively, in the pol gene region, which corresponds to a gene expression repressive region derived from HTLV-I. On the other hand, HIV did not exhibit high homology in certain regions. Therefore, it is considered that 59% homology is preferable for a sequence having similar activity to that of the gene expression repressive region derived from HTLV-I.

Example 4

Cancellation of the Gene Expression Repression Activity Derived from HTLV-I with RRE-dependent Rev The relationship between Rex and RXE is known of HTLV-I. Similarly, the relationship between Rev and RRE is known of HIV. Therefore, in accordance with the description of (3) of Example 2, plasmids (CMV-CAT-R7-RRE (+ or −), CMV-CAT-R8-RRE (+ or −), and CMV-CAT-R21-RRE (+ or −)) were constructed by incorporating RRE, instead of RXE, in the sense (+) or antisense (−) orientation immediately 3' downstream of the respective genomic regions in CMV-CAT-R7, CMV-CAT-R8, and CMV-CAT-R21 so as to be transcribed to RNA. HeLa cells were co-transfected with 2 µg each of these plasmids and 1.5 µg of an SRα-rev plasmid expressing Rev protein or 1.5 µg of a pCD-SRα plasmid not expressing Rev protein, and the CAT activity thereof was measured. The results are shown in Table 2.

TABLE 2

| plasmid | Rev | CAT activity(%) | fold induction (Rev+/Rev−) |
|---|---|---|---|
| CMV-CAT-R7-RRE(+) | + | 13.1 | 10.0 |
| | − | 1.3 | |
| CMV-CAT-R7-RRE(−) | + | 1.5 | 1.3 |
| | − | 1.2 | |
| CMV-CAT-R8-RRE(+) | + | 2.9 | 5.0 |
| | − | 0.58 | |
| CMV-CAT-R8-RRE(−) | + | 0.48 | 1.1 |
| | − | 0.42 | |
| CMV-CAT-R21-RRE(+) | + | 42.6 | 1.6 |
| | − | 26.5 | |
| CMV-CAT-R21-RRE(−) | + | 33.9 | 0.74 |
| | − | 45.7 | |

AS can be seen from Table 2, the R7 and R8 regions strongly repressed the expression of the CAT gene regardless of the orientations in which RRE was incorporated. The repression effects were compared based on a fold induction, which is a value obtained by dividing the CAT activity (%) in the case of Rev+ by the CAT activity in the case of Rev−. Thus, it was revealed that the effect of Rev protein is exhibited only when RRE is incorporated in the sense orientation. This result was similar to the result in (3) of Example 2.

Example 5

Cloning of TRP-1 cDNA

In order to isolate a factor that binds to the transcriptional repressive sequence U5RE present in U5, a Molt-4 cDNA library was screened by the South-Western method by using a DNA including having eight U5REs linked as a probe.

In order to prepare a probe for screening by the South-Western method, oligonucleotides for both strands corresponding to U5RE (SEQ ID NO:17 and SEQ ID NO:18 in the Sequence Listing) were synthesized. After the synthesized DNA was subjected to electrophoresis for 2 hours at 300 V by using gel including 19% acrylamide, 1% acrylamide/bis, and 7 M urea, gel containing the synthetic DNA of interest was cut. Next, the gel was immersed in TE buffer (10 mM Tris-HCl, ph 7.4, 1 mM EDTA) for 16 hours at 37° C., whereby DNA was eluted from the gel. The eluate was passed through DE52 (manufactured by Pharmacia Biotech.) saturated with TE buffer for adsorbing DNA. Thereafter, elution was performed by using 0.5 ml of TNE buffer (10 mM Tris-HCl, pH 7.4, 1 mM EDTA, and 1.5 M NaCl). One ml of ethanol was added to the DNA solution and the DNA was precipitated, whereby the synthetic DNA was purified. The purified synthetic DNA was dissolved in TE buffer. Each of the DNA was added to a solution to a final concentration of 10 µg/µl and then heat-denatured at 65° C. for 10 minutes and thereafter gradually cooled, thereby forming double-stranded DNA. Next, 100 units of ligase (manufactured by Nippon Gene Co., Ltd.) was added to 1 µg of the double-stranded DNA, allowed to react at 12° C. for 16 hours, thereby linking eight U5REs. The resultant DNA (8×U5RE) was incorporated at the BamHI and BglII sites of a plasmid pSL1180 (manufactured by Pharmacia Biotech.) through a 16-hour ligation at 12° C. in the presence of 10 units of ligase.

A probe to be used for the South-Western method was amplified by PCR in the presence of $\alpha^{32}$P-dCTP using the above-mentioned 8×U5RE as a template. The PCR reaction solution was obtained by placing 1 µl of 8×U5REpSL1180 (1 ng/µl) into 2 µl of 10×PCR buffer (100 mM Tris-HCl, pH 8.3, 500 mM KCl, 15 mM $MgCl_2$, 0.1% gelatine), 1 µl of dNTPs (4 mM dATP, 4 mM dGTP, 4 mM dTTP, 0.8 mM dCTP), 0.5 µl of Taq polymerase (manufactured by Takara Shuzo Co., Ltd., 5 units/µl), 1 µl each of synthetic primer (pSL F; SEQ ID NO:19 in the Sequence Listing, pSL R; SEQ ID NO:20 in the Sequence Listing: 10 pmol/µl), 12.5 µl of $\alpha^{32}$P-dCTP, and sterilized distilled water to 20 µl. The PCR was performed using Thermal sequencer TSR-300 (Iwaki Glass Co., Ltd.). After the reaction was performed for 60 seconds at 94° C., a reaction cycle of 45 seconds at 94° C., 45 seconds at 55° C., and 45 seconds at 72° C. was repeated 35 times, followed by 60 seconds at 72° C.

A cDNA library of the human acute lymphocytic leukemia cell line Molt-4 in pSport 1 was made as follows: First, after 1 ml of 4 M guanidine thiocyanate was added, $10^9$ Molt-4 cells were extracted by adding 1 ml of phenol saturated with water. Total RNA was obtained by extracting this extract using 1 ml of isopropanol. From 100 μg of the total RNA, 10 μg of mRNA was obtained by using Oligotex. From the 10 μg of mRNA, CDNA was made by using Superscript CDNA Synthesis System (manufactured by GIBCO-BRL Inc.) and then cDNA libraries (pSPORT-1 (manufactured by BRL Inc.)) were made.

Next, the cDNA library of Molt-4 was introduced into *E. coli* DH5α and plated at 50,000 colonies per petri dish, so that a total of 2,000,000 colonies was subjected to screening. The colonies thus plated were allowed to contact with nitrocellulose membranes (manufactured by Millipor Ltd.) for 1 minute. The nitrocellulose membranes were incubated on a medium containing 1 mM of IPTG (manufactured by GIBCO-BRL Inc.) at 37° C. for 3 hours, whereby proteins were expressed. The proteins produced from the thus-prepared cDNA immobilized to nitrocellulose membranes were reacted with the above-mentioned probe, and subjected to screening by using the proteins' DNA binding activity as an indicator.

Furthermore, the cDNA fragments prepared from the resultant cDNA clones were used as probes for screening a $10^6$ Molt-4 cDNA library by colony hybridization. A filter was prepared by transferring colonies which were cultured overnight at 37° C. on an agar medium to a Colony/PlaqueScreen Plus filter (manufactured by Du Pont Ltd.), and thereafter immersed in 0.5 M NaOH, 1.5 M NaCl for a minute, 0.5 M Tris-HCl, 1.5 M NaCl for 5 minutes, and 2×SSC for 5 minutes and air dried. The probe was radiolabelled with $\alpha^{32}$P-dCTP by using a Multiprime Labelling Kit (manufactured by Amersham, Inc.). The hybridization was performed as follows: after a prehybridization with 6×SSPE (0.9 M NaCl, 0.06 M sodium phosphate, 6 mM EDTA, pH 7.4), 10% Irish cream (manufactured by R&A BAILEYS Inc.), 1% SDS, and 50% formamide at 42° C. for 6 hours without a probe, a probe was added and a 16-hour hybridization was performed at 42° C. The filter was washed with 1×SSC 0.5% SDS for 10 minutes at room temperature and twice with 0.2×SSC 0.5% SDS for 30 minutes at 65° C. The signal was detected by a 16-hour exposure at −80° C. using an X-ray film (manufactured by Eastman Kodak Co.; XAR5) in the presence of an intensifying screen, followed by development.

Figure 10:
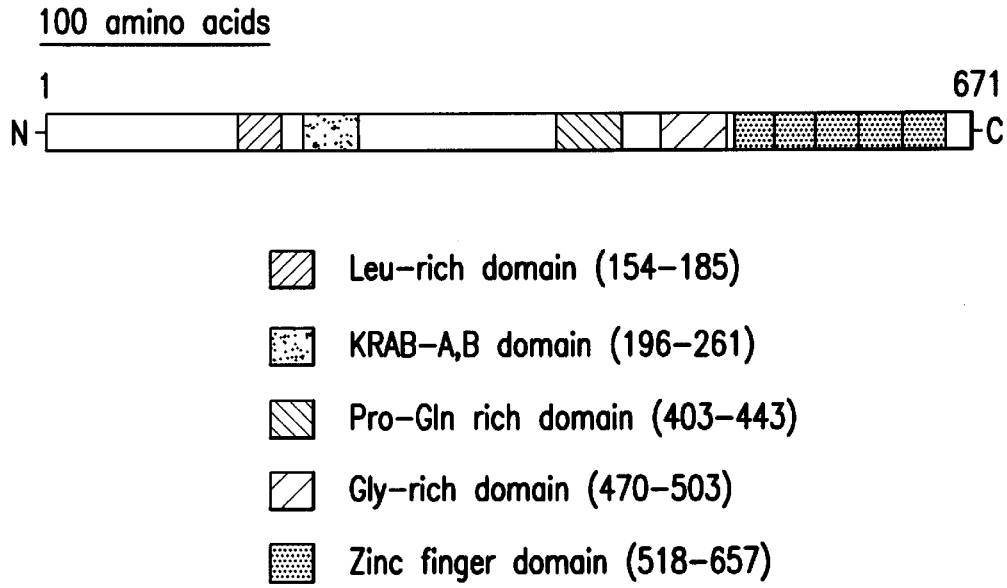
FIG. 10 is a schematic diagram showing the domain structure of the TRP-1 protein according to the present invention.

As a result, a positive clone including a cDNA insert of about 3.8 kb was obtained. The base sequence of the resultant cDNA clone was determined following a dideoxy method (Sanger, supra) by using a Sequenase DNA Sequencing Kit (U.S.B. Inc.). The determined DNA sequence and amino acid sequence are shown as SEQ ID NO: 15 in the Sequence Listing. A deduced amino acid sequence based on a base sequence obtained by analyzing this cDNA fragment was analyzed (DNASIS (Hitachi Software Engineering Co., Ltd.)). As a result of the computer analysis, it was found that this gene is a novel gene, whose longest open reading frame can be translated into an amino acid sequence of 671 amino acids. From this amino acid sequence, as shown in FIG. 10, it was found that there are five zinc finger-like domains at the carboxyl end, which are Kruppel-type DNA binding regions, and a pair of KRAB-A,B-like domains at the amino end, which are transcription regulatory regions. Moreover, the putative molecular weight based on the amino acid sequence is 76 kDa, indicative of a clear difference in terms of molecular weight and characteristic domains from known proteins (110 kDa, 80 kDa, and 70 kDa) which specifically bind to U5RE.

Furthermore, through similarity analysis, the gene having an amino acid sequence which had the highest similarity was shown to be Kid-1 (Witzgall et al., Mol. Cell. Biol. 13(3): 1933–1942(1993), supra). Based on a comparison at the amino acid sequence level, as shown in FIG. 11, its zinc finger domains (corresponding to amino acids at positions 518–657 of TRP-1, and positions 407–529 of Kid-1) showed 61.0% similarity and 53.7% homology. As shown in FIG. 12, the KRAB-A,B domains (amino acids at positions 196–261 of TRP-1 and positions 12–53 of Kid-1) showed 48.5% similarity and 34.9% homology.

As for the characteristic sequences other than the above, it was found that a leucine-rich domain containing 34.4% leucine is present at amino acids 154–185; a proline/glutamine-rich domain containing 65.9% proline/glutamine is present at amino acids 403–443; and a glycine-rich domain containing 58.8% glycine is present at amino acids 470–503. It is known that the proline/glutamine-rich domain is involved in protein-protein interactions, but the functions of the other domains have not been revealed yet.

Example 6

Expression of Recombinant TRP-1 and Analysis of its Nature

In order to express TRP-1, pRSET-TRP-1 was constructed by inserting a DNA fragment of 3.8 kb obtained by cleaving with KpnI and NotI the DNA of a cDNA clone, which in itself was obtained by expression cloning, into the KpnI-NotI site of an expression vector pRSET (manufactured by Invitrogen Inc.). *E. coli* BL12 strain, into which pRSET-TRP-1 had been introduced, was capable of expressing TRP-1 as a fusion protein having oligohistidine at its amino terminus. After the bacterium was cultured overnight at 30° C. in 2L of LB medium, IPTG was added to a final concentration of 1 mM, and 6 more hours of culture was conducted. The fusion protein was purified by an affinity column method using a plate bond resin (Invitrogen Inc.). Furthermore, it was separated through electrophoresis using a Prep-cell (manufactured by BIO-RAD Inc.) to give a final purified product.

The binding analysis between TRP-1 and U5RE was made as follows: First, 1 ng of U5RE DNA labelled with $^{32}$P and the above-mentioned recombinant TRP-1 were reacted in a binding reaction buffer (20 mM Tris-HCl, 1 mM EDTA, 50 mM NaCl, 1 mM DTT, and 5% glycerol) for 30 minutes at room temperature in the presence of 1 μg poly d(I-C). Next, the reaction solution was subjected to electrophoresis on 5% polyacrylamide gel and dried on a paper filter, and thereafter analyzed through autoradiography.

Figure 13:
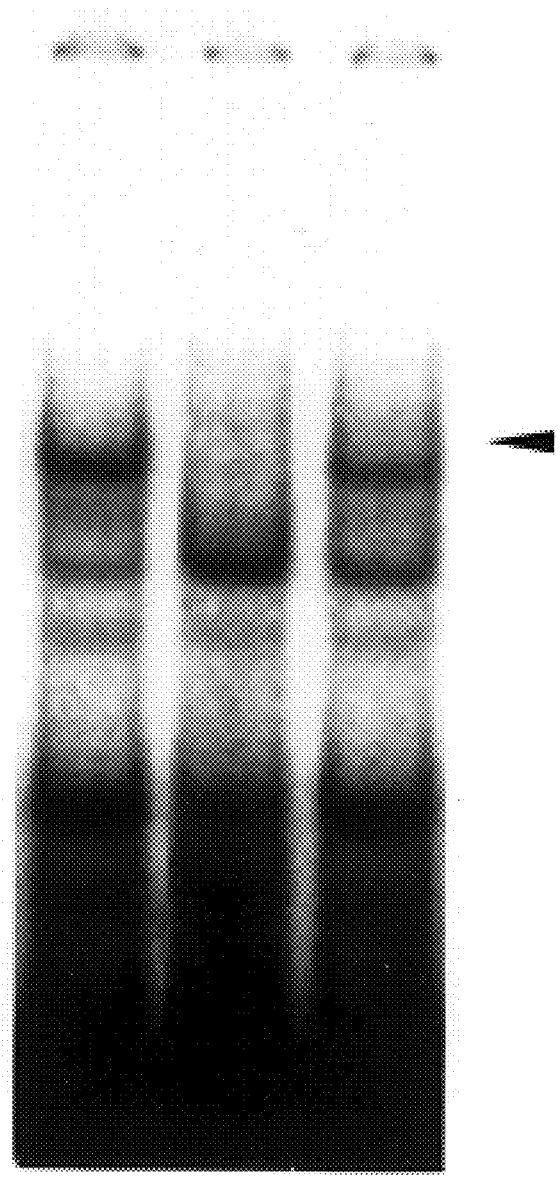
FIG. 13 shows results of an electrophoresis of binding specificity analysis by a gel shift assay of the TRP-1 protein according to the present invention expressed by using *E. coli*.

The results of the binding analysis between TRP-1 and U5RE are shown in FIG. 13. Lane 1 in FIG. 13 represents the result of the binding reaction between TRP-1 expressed from *E. coli* and the U5RE probe; lane 2 represents the result of the case where non-labelled U5RE in a molar amount 100 times relative to the U5RE probe was added to the reaction solution of lane 1; and lane 3 represents the result of the case where 100 times molar amount of a non-specific DNA fragment was added instead of the U5RE of lane 2. It was indicated that this recombinant TRP-1 binds to the U5RE DNA labelled with 32P. In addition, competitive reactions were attempted for the U5RE DNA probe, using non-labelled U5RE DNA or a DNA non-related to the base sequence of the U5RE DNA having the same length, which revealed competition only with the non-labelled U5RE DNA. Thus, it was discovered that this TRP-1 specifically binds to the U5RE DNA.

Example 7

Tissue Distribution of TRP-1 mRNA Expression

In order to examine the distribution of TRP-1 expression with respect to different tissues, we conducted a Northern blot analysis was conducted using RNA from human cell lines (28 lines) and tissues (16 sites).

First, 3 μg of poly(A)+RNA isolated from each cell was subjected to electrophoresis on 1% agarose gel containing 0.66 M formaldehyde in a MOPS buffer solution (20 mM MOPS, pH 7.0, 5 mM sodium acetate, 0.5 mM EDTA), transferred to a nylon membrane (Gene Screen Plus, manufactured by Du Pont Ltd.) by capillary transfer using 20×SSC, and the nylon membrane was air dried. A hybridization was performed using this filter and a commercially available filter (manufactured by Clontech Inc.) on which mRNAs derived from human tissues are blotted, using as a probe TRP-1 cDNA (bases to position 950 from the 5' end of the fragment obtained by expression cloning) labelled with $\alpha^{32}$P-dCTP by using a Multiprime Labelling Kit (manufactured by Amersham, Inc.), in a hybridization buffer (6×SSPE, 1%, SDS, 10% Irish cream (manufactured by R&A BAILEYS Inc.), and 50% formamide). The filters were washed with 1×SSC 0.5% SDS for 10 minute s at room temperature and twice with 0.2×SSC 0.5% SDS for 30 minutes at 65° C. The signal was detected by a 16-hour exposure at −80° C. using an X-ray film (manufactured by Eastman Kodak Co.; XAR5) in the presence of an intensifying screen, followed by development.

Figure 14:
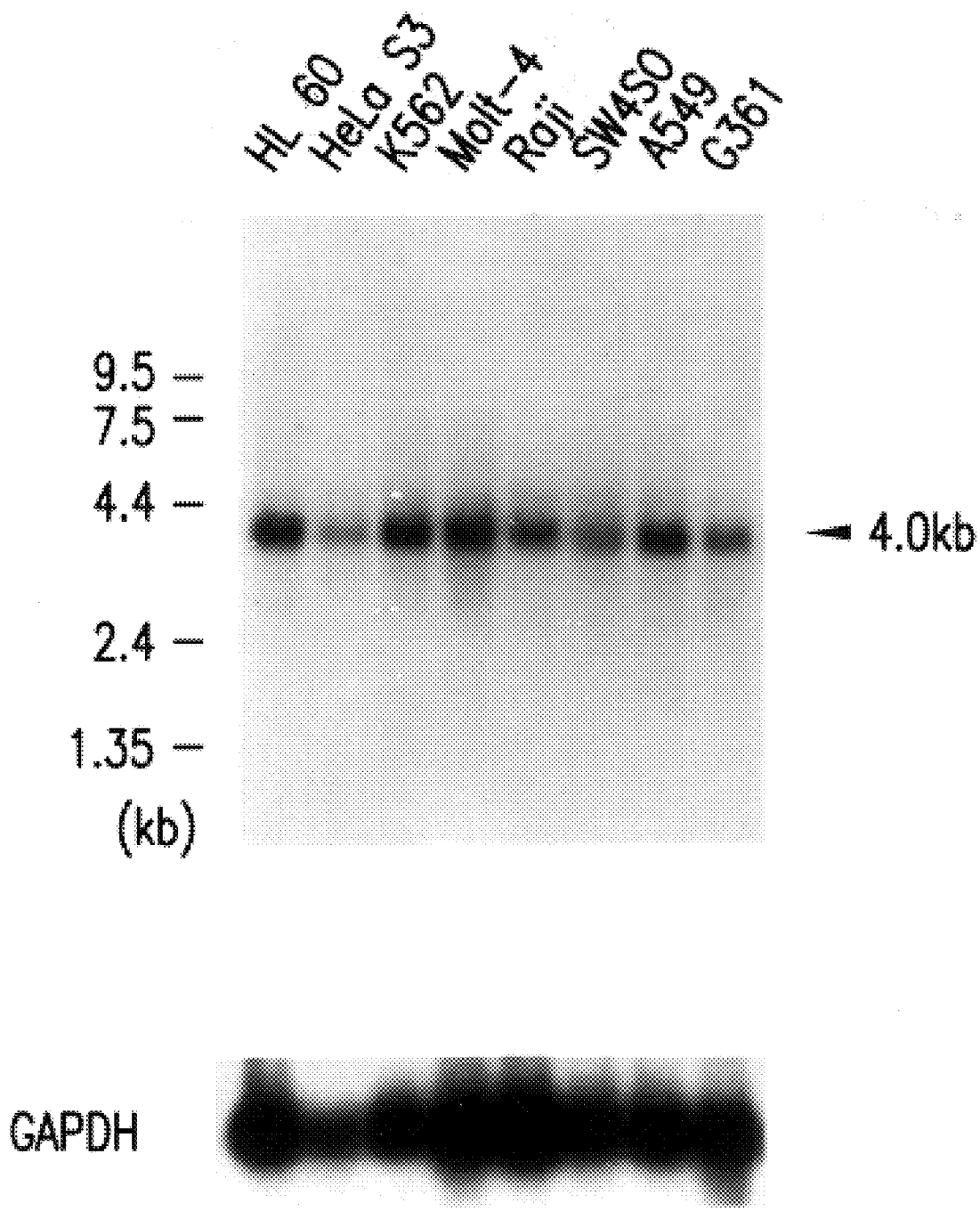
FIG. 14 shows results of an electrophoresis of a Northern blotting analysis of the expression of mRNA of the TRP-1 according to the present invention in various culture cells.
Figure 15:
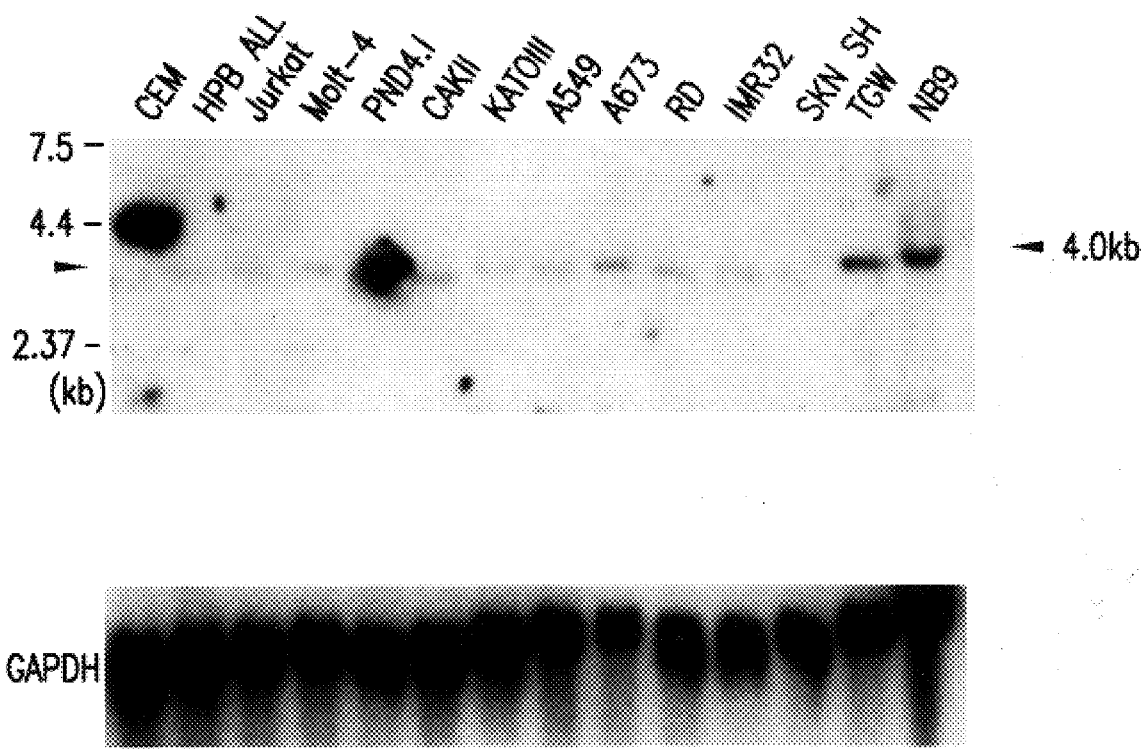
FIG. 15 shows results of an electrophoresis of a Northern blotting analysis of the expression of mRNA of the TRP-1 according to the present invention in various culture cells.

FIGS. 14 and 15 show the results for the respective cell lines. FIG. 14 shows the Northern blotting results of the respective cell lines of HL60 (acute myelogenous leukemia), HeLa cell S3 (cervical cancer), K-562 (chronic myelogenous leukemia), Molt-4 (acute lymphocytic leukemia), Raji (Burkitt's lymphomas), SW480 (colon adenocarcinomas), A549 (lung cancer), and G361 (melan omas). FIG. 15 shows the Northern blotting results of th e respective cell lines of CEM, HPB, Jurkat, Molt-4, PND4.1 (all of which ar e from acute lymphocytic leukemia), CAKII (kidney cancer), KATO III (stomach cancer), A549 (lung cancer), A673 and RD (both of which are from rhabdomyosarcomas), IMR32, SKN SH, TGW, and NB9 (all of which are from neuroblastomas). Expression of a transcript of 4.0 kb, see arrow in FIG. 15, was found in the cell lines, regardless of whether they were HTLV-I infected T cells or non-infected T cells. The expression of the TRP-1 gene was found in all the cell lines subjected to the experiment. Two out of the four kinds of neuroblastoma cells (TGW and NB9) showed an expression level 5 times to 10 times higher than that of the other neuroblastoma cells and the other cells. Furthermore, the expression by neuroblastoma cell lines GOTO, CHP134, NB19, and NB16, and glioma cell lines A2781, U251, and T98G was examined, revealing a high expression by GOTO and NB19 (data not shown). Accordingly, it was found that four lines out of the 8 neuroblastoma cell lines subjected to the study showed a high expression of the mRNA for TRP-1.

Figure 16A:
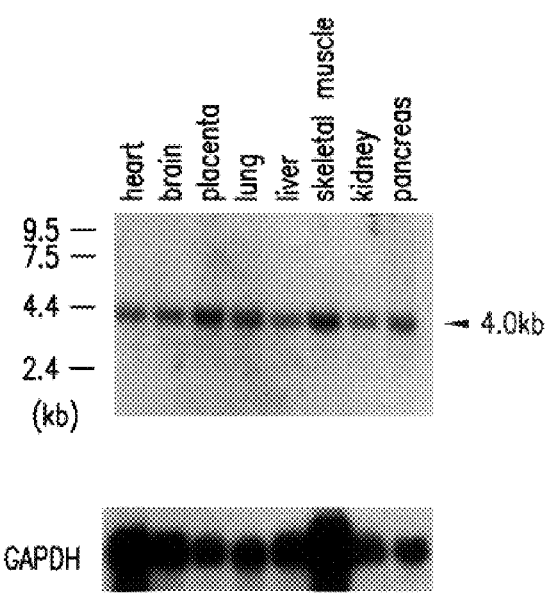
FIGS. 16(A) and (B) show results of electrophoreses of Northern blotting analyses of the expression of mRNA of the TRP-1 according to the present invention in respective tissues.
Figure 16B:
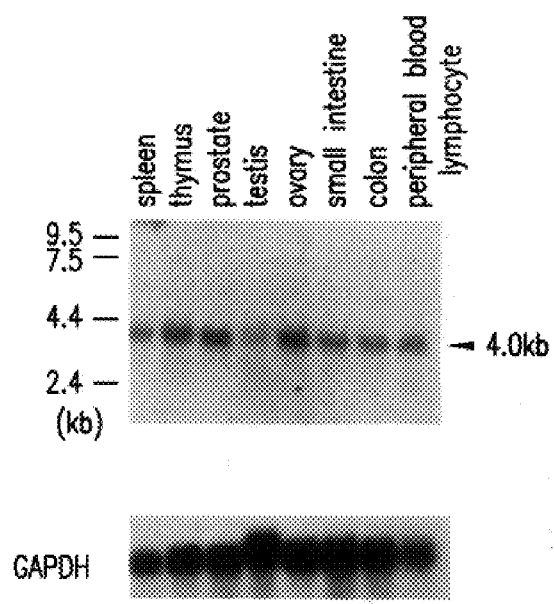

Next, FIGS. 16(A) and (B) show the results of the respective tissues. It was found that a substantially constant level of expression is shown by tissues other than the testis, which showed an extremely low level of expression. Thus, since normal brain tissues do not show a particularly high expression of the mRNA of TRP-1 as compared with other tissues, the results showing high expression by the neuroblastoma cell lines indicate a close relationship with oncogenesis of neurocytes in part.

Example 8

Functional Analysis of TRP-1

A functional analysis of TRP-1 was conducted as follows. An expression vector pEF-HA-TRP-1 obtained by engineering an EF-BOS vector so that a HA-TRP-1 fusion protein having the influenza HA tag at the N-terminus of TRP-1 would be expressed, and a reporter plasmid TK-CAT in which HSV TK (a minimum promoter region) was linked upstream of the CAT (chloramphenicol acetyl transferase) gene or TK-3×U5RE-CAT in which three U5REs were inserted between the TK and CAT genes, were simultaneously introduced into HeLa cells using Lipofectin (manufactured by GIBCO-BRL Inc.). The TK-3×U5RE-CAT includes U5REs, which are binding sequences for TRP-1, whereas TK-CAT includes no binding sequences. After a 48-hour culture, the cells were recovered, homogenized and centrifuged, and the proteins in the supernatant were quantitated. To 100 μg were added 4 μl of [$^{14}$C] chloramphenicol (manufactured by Amersham, Inc.) and 10 μl of 4 mM of acetyl CoA (manufactured by Sigma, Inc.). After a 1-hour incubation at 37° C. and addition of 0.5 ml of ethyl acetate followed by stirring, a centrifugation at 10,000 rpm was performed for 10 seconds to recover a layer of ethyl acetate. The ethyl acetate layer was dried and again dissolved in 20 μl of ethyl acetate, spotted on a silica gel thin-layer plate (DC-Alufolien Kiesel gel 60 F254, manufactured by MERCK & Co., Inc.), and developed in a thin layer chamber with a solvent of chloroform-ethanol (95:5). The acetylation rate of this developed silica gel thin-layer plate was examined by using a BioImage Analyzer (manufactured by Fujix Ltd.) to examine the activity of the CAT that was present.

Figure 17:
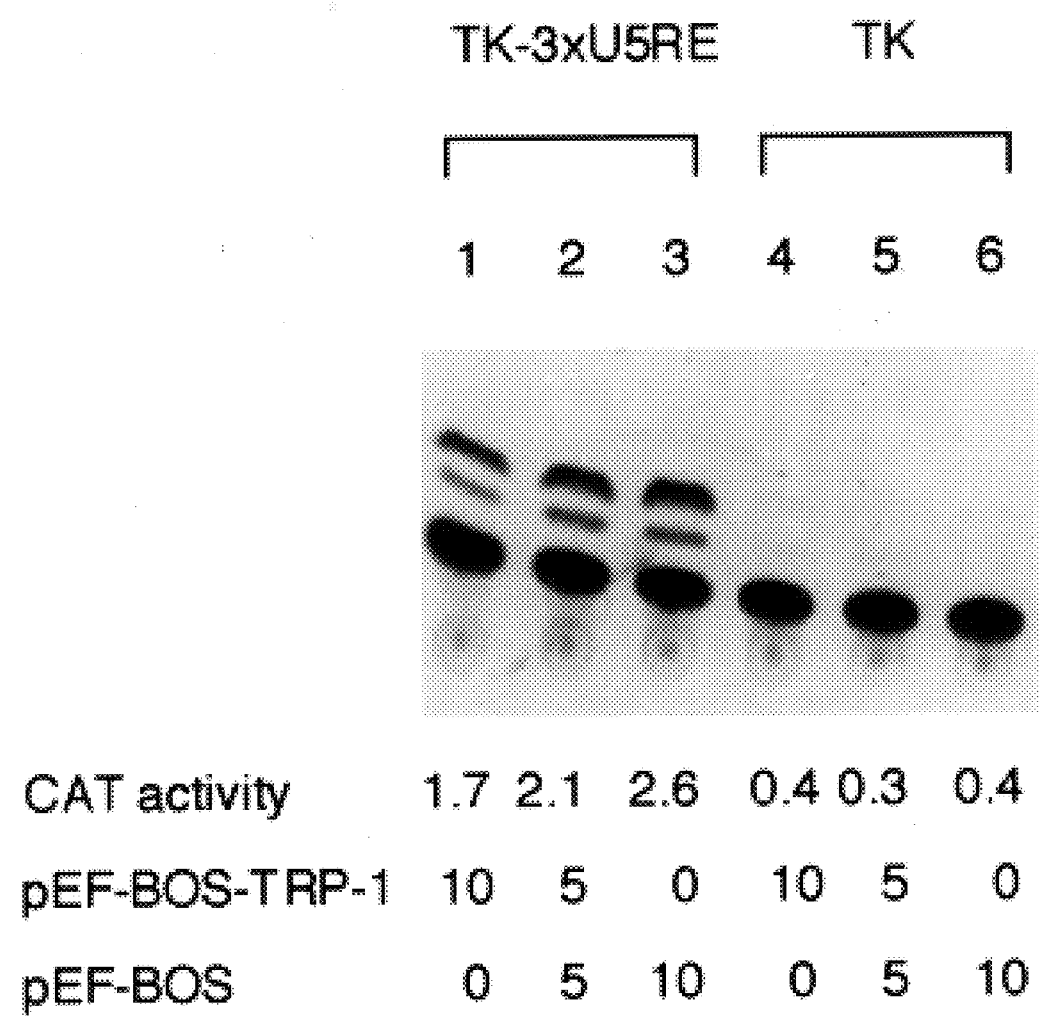
FIG. 17 shows results of functional analyses of the TRP-1 protein according to the present invention for U5RE in a CAT assay.

The results are shown in FIG. 17. The following lanes of FIG. 17 show the analysis results, where the analysis was conducted using an extract of the cells recovered after 48 hours: Lanes 1 to 3 used 2 μg of TK-3×U5RE-CAT as a reporter gene; lanes 4 to 6 using 2 μg of TK-CAT. Furthermore, as an effector gene, lanes 1 and 4 used 10 μg of pEF-BOS-TRP-1; lanes 2 and 5 used 5 μg of pEF-BOS-TRP-1+5 μg of pEF-BOS; and lanes 3 and 6 used 10 μg of pEF-BOS, each introduced into HeLa cells. In other words, a pair consisting of pEF-HA-TRP-1 and TK-3×U5RE-CAT or a pair consisting of pEF-HA-TRP-1 and TK-CAT was introduced into HeLa cells so as to analyze whether or not TRP-1 functions via U5RE. As a result, the CAT activity by TK-3×U5RE-CAT was reduced by 35% in a concentration-dependent manner based on the concentration of the pEF-HA-TRP-1 plasmid, whereas no effect was observed for TK-CAT. Thus, it was indicated that TRP-1 has transcription repression activity via U5RE.

INDUSTRIAL APPLICABILITY

The present invention provides DNA molecules and proteins associated with a gene expression repressing function.

The DNA molecules having a gene expression repressing function derived from HTLV-I according to the present invention is capable of allowing virus-infected cells to avoid elimination by the immune system by repressing the expression of a viral gene within an organism, thereby playing an important role in the latent infection mechanism of HTLV-I. It is contemplated that, by successfully utilizing this gene expression repression action and the cancellation thereof by the Rex protein, it becomes possible to artificially control the gene expression, which can be applied to cell-specific gene expression in gene therapies and the like.

Figure 9:
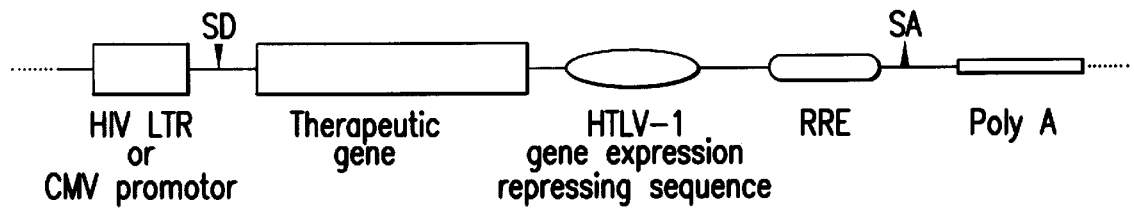
FIG. 9 is a schematic diagram showing constituent units in a plasmid for gene therapy of HIV infectious diseases (e.g., AIDS).

It is also contemplated that the invention can be applied to gene therapies for HIV infectious diseases (e.g., AIDS) by using a plasmid including a DNA sequence having the gene expression repression function according to the present invention including constituent units such as those shown in FIG. 9. For example, constituent units such as those shown in FIG. 9 can be incorporated into a retrovirus vector and introduced into an infected or non-infected cell. In the case where it is introduced into a non-infected cell, the gene expression repressive DNA sequence functions so that the expression of the therapeutic gene is repressed. Furthermore, by disposing a splice donor (SD) signal and a splice acceptor (SA) signal, the therapeutic gene, and the like, is removed through splicing, whereby the expression of the therapeutic gene is further repressed. On the other hand, in the case of an infected cell, the Rev protein is expressed by the HIV gene, which cancels the repression activity of the gene expression repressive sequence via RRE, whereby the expression of the therapeutic gene is promoted. Furthermore, by using HIV LTR as a promoter, the expression of the therapeutic gene is further enhanced by the transcription enhancing function of the Tat protein of HIV.

It is also contemplated that the DNA molecules having the gene expression repressing function according to the present invention and plasmid including the DNA molecules are effective for elucidation of the onset mechanism of diseases such as adult T-cell leukemia (ATL), HTLV-I associated myelopathy (HAM), and tropical spastic paraparesis (TSP) and the development of effective therapeutics therefor.

The TRP-1 according to the present invention is a DNA binding protein which specifically binds to U5RE, and has transcription repression activity. Therefore, it is considered to affect the expression repression of genes having a similar sequence, e.g., the genes of human immunodeficiency virus, cytomegalovirus or cellular genes. Therefore, it is likely to possess antiviral activities, and can be applied to the development of antiviral agents.

Kid-1, which has relatively high similarity to TRP-1, has been isolated from rat kidneys, and it is known that the expression of mRNA for Kid-1 increases to repress transcription in the development process of kidneys, upon ischemia, or in the regeneration process of renal tissues after a folic acid treatment. Therefore, since TRP-1 is expressed in most tissues or cell lines, it is considered to have physiologically important activity which is associated with transcription repression. That is, the protein according to the present invention can be useful as an effective component of an antiviral agent.

Furthermore, the extraordinarily high expression of TRP-1 observed in half of the neuroblastoma cell lines indicates its involvement in the oncogenesis mechanism of neurocytes. Therefore, studying TRP-1 can be useful for elucidation of mechanism, diagnosis, and treatment of the oncogenesis of neurocytes. In other words, the expression of the protein according to the present invention within a tissue can serve as an indicator for detecting the carcinogenesis. Furthermore, the protein according to the present invention or the antisense strand of a DNA molecule encoding the protein according to the present invention can become a therapeutic agent for cancer.

What is claimed is:

1. A protein which binds to a transcriptional repressive region existing in the U5 region of human T-cell leukemia virus type I gene LTR, the protein comprising a domain common to Kruppel-type transcriptional repressive factors and five Kruppel-type zinc finger domains, wherein the protein comprises an amino acid sequence from Met at position 1 to Asp at position 671 of SEQ ID NO:15, or a sequence having a similarity thereto of about 80% or more, or having a homology thereto of about 65% or more.

2. The protein according to claim 1 having a molecular weight of about 76 kDa.

3. A protein which binds to a transcriptional repressive region existing in the U5 region of human T-cell leukemia virus type I gene LTR, the protein comprising a domain common to Kruppel-type transcriptional repressive factors and five Kruppel-type zinc finger domains, wherein the domain common to Kruppel-type transcriptional repressive factors is an amino acid sequence from Val at position 196 to Trp at position 261 of SEQ ID NO:15, or a sequence having a similarity thereto of about 80% or more, or having a homology thereto of about 65% or more, and the five Kruppel-type zinc finger domains are an amino acid sequence from Tyr at position 518 to Gly at position 657 of SEQ ID NO:15, or a sequence having a similarity thereto of about 80% or more, or having a homology thereto of about 65% or more.

4. The protein according to claim 3 further comprising an amino acid sequence from Leu at position 154 to Leu at position 185 of SEQ ID NO:15, an amino acid sequence from Pro at position 403 to Pro at position 443 of SEQ ID NO:15, and an amino acid sequence from Arg at position 470 to Gly at position 503 of SEQ ID NO:15, or sequences having a similarity of about 80% or more, or having a homology of about 65% or more, to such amino acid sequences.

5. An antiviral agent containing the protein according to any one of claims 1 to 4 as an effective ingredient.

* * * * *

UNITED STATES PATENT AND TRADEMARK OFFICE
CERTIFICATE OF CORRECTION

PATENT NO   : 6,090,783
DATED       : July 18, 2000
INVENTION(S): DNA MOLECULE RELATING TO SUPPRESSION OF GENE EXPRESSION AND NOVEL PROTEIN It is certified that error appears in the above-identified patent and that said Letters Patent is hereby corrected as shown below:

Column 51, line 18, delete "SEQ ID NO:15" and substitute therefor -- SEQ ID NO:16 --.
Column 51, line 30, delete "SEQ ID NO:15" and substitute therefor -- SEQ ID NO:16 --.
Column 52, line 15, delete "SEQ ID NO:15" and substitute therefor -- SEQ ID NO:16 --.
Column 52, line 20, delete "SEQ ID NO:15" and substitute therefor -- SEQ ID NO:16 --.
Column 52, lines 21-22, delete "SEQ ID NO:15" and substitute therefor
-- SEQ ID NO:16 --.
Column 52, line 23, delete "SEQ ID NO:15" and substitute therefor -- SEQ ID NO:16 --.

Signed and Sealed this

Seventeenth Day of April, 2001

*Attest:*

NICHOLAS P. GODICI

*Attesting Officer*        *Acting Director of the United States Patent and Trademark Office*